United States Patent
Payne et al.

(10) Patent No.: US 12,409,228 B2
(45) Date of Patent: Sep. 9, 2025

(54) HYDROGEL DRUG DELIVERY SYSTEMS FOR THE TREATMENT OF PEDIATRIC GROWTH PLATE INJURIES

(71) Applicants: THE REGENTS OF THE UNIVERSITY OF COLORADO, A BODY CORPORATE, Denver, CO (US); COLORADO SCHOOL OF MINES, Golden, CO (US)

(72) Inventors: Karin A. Payne, Denver, CO (US); Melissa D. Krebs, Englewood, CO (US)

(73) Assignees: The Regents of the University of Colorado, a body corporate, Denver, CO (US); Colorado School of Mines, Golden, CO (US)

( * ) Notice: Subject to any disclaimer, the term of this patent is extended or adjusted under 35 U.S.C. 154(b) by 0 days.

(21) Appl. No.: 18/392,543

(22) Filed: Dec. 21, 2023

(65) Prior Publication Data

US 2024/0238421 A1    Jul. 18, 2024

Related U.S. Application Data

(63) Continuation of application No. 16/762,860, filed as application No. PCT/US2018/059460 on Nov. 6, 2018, now abandoned.

(60) Provisional application No. 62/583,047, filed on Nov. 8, 2017.

(51) Int. Cl.
| | |
|---|---|
| A61K 47/36 | (2006.01) |
| A61B 17/16 | (2006.01) |
| A61K 9/00 | (2006.01) |
| A61K 9/06 | (2006.01) |
| A61K 47/22 | (2006.01) |
| A61L 27/20 | (2006.01) |
| A61L 27/52 | (2006.01) |
| A61L 27/54 | (2006.01) |
| A61P 19/00 | (2006.01) |
| A61P 19/08 | (2006.01) |
| A61P 19/10 | (2006.01) |
| C07K 16/22 | (2006.01) |
| C08J 3/075 | (2006.01) |

(52) U.S. Cl.
CPC ............ *A61K 47/36* (2013.01); *A61K 9/0019* (2013.01); *A61K 9/06* (2013.01); *A61K 47/22* (2013.01); *A61L 27/20* (2013.01); *A61L 27/52* (2013.01); *A61L 27/54* (2013.01); *A61P 19/00* (2018.01); *A61P 19/08* (2018.01); *C07K 16/22* (2013.01); *C08J 3/075* (2013.01); *A61B 17/16* (2013.01); *A61L 2300/256* (2013.01); *A61L 2300/412* (2013.01); *A61L 2300/414* (2013.01); *A61L 2300/416* (2013.01); *A61L 2300/62* (2013.01); *A61L 2430/06* (2013.01); *A61P 19/10* (2018.01); *C08J 2305/04* (2013.01); *C08J 2305/08* (2013.01)

(58) Field of Classification Search
None
See application file for complete search history.

(56) References Cited

U.S. PATENT DOCUMENTS

| | | |
|---|---|---|
| 8,900,630 B2 | 12/2014 | Yan |
| 2007/0005140 A1 | 1/2007 | Kim et al. |
| 2008/0029390 A1* | 2/2008 | Roche ............... A61B 5/14532 435/14 |
| 2011/0091570 A1 | 4/2011 | Gottardi |
| 2013/0316007 A1 | 11/2013 | Ma et al. |
| 2014/0377366 A1 | 12/2014 | Krebs |
| 2015/0283287 A1 | 10/2015 | Agarwal |
| 2017/0096479 A1 | 4/2017 | Koenig et al. |

FOREIGN PATENT DOCUMENTS

| | | |
|---|---|---|
| WO | 2017040537 A1 | 3/2017 |
| WO | 2017152112 A2 | 9/2017 |

OTHER PUBLICATIONS

Fletcher et al., "Cell-interactive alginate-chitosan biopolymer systems with tunable mechanics and antibody release rates", Carohydrate Polymers 175 (2017): 765-772.
Lankalapall et al., "Polyelectrolyte Complexes: A Review of their Applicability in Drug Delivery Technology", Indian J. Pharm. Sci., (2009), 71(5): 481-487.
Tan et al., "Injectable In Situ Forming Biodegradable Chitosan-Hyaluronic acid Based Hydrogels for Cartilage Tissue Engineering", Biomaterials (2009); 30(13): 2499-2506.
Tyagi et al., "Minimizing the negative charge of Alginate facilitates the delivery of negatively charged molecules inside cells," Journal of Polymer Research, vol. 29, No. 1, 2022.

* cited by examiner

*Primary Examiner* — Sin J Lee
(74) *Attorney, Agent, or Firm* — Polsinelli PC

(57) ABSTRACT

The present invention relates to the unexpected discovery of compositions and methods for the treatment of growth plate defects. In certain embodiments, the methods prevent the growth of "bony bars" at the site of growth plate injury, thereby preventing growth arrest and/or deformity. In certain embodiments, the compositions comprise hydrogels comprising at least one biological factor capable of preventing bony bar formation.

19 Claims, 21 Drawing Sheets

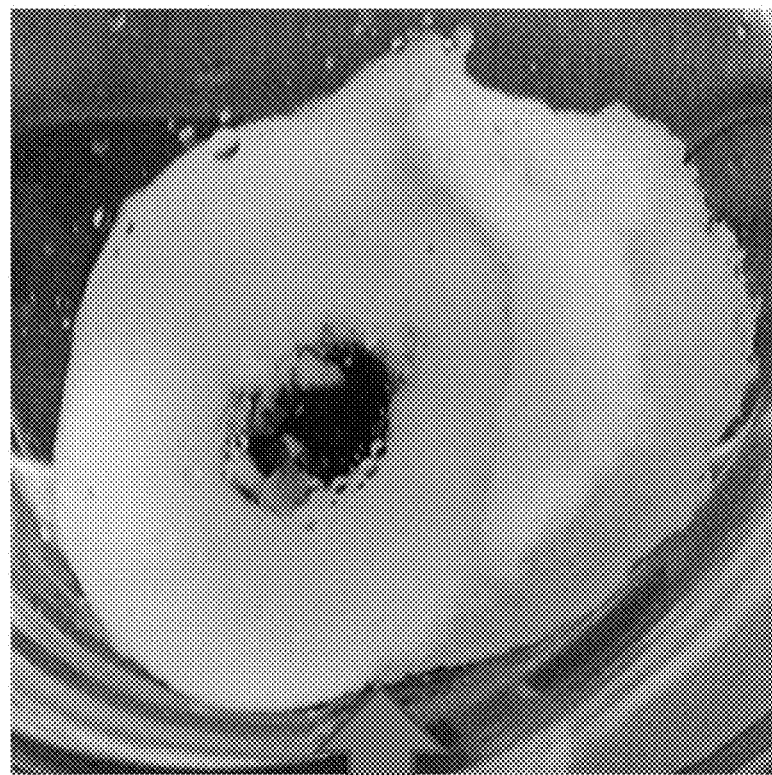
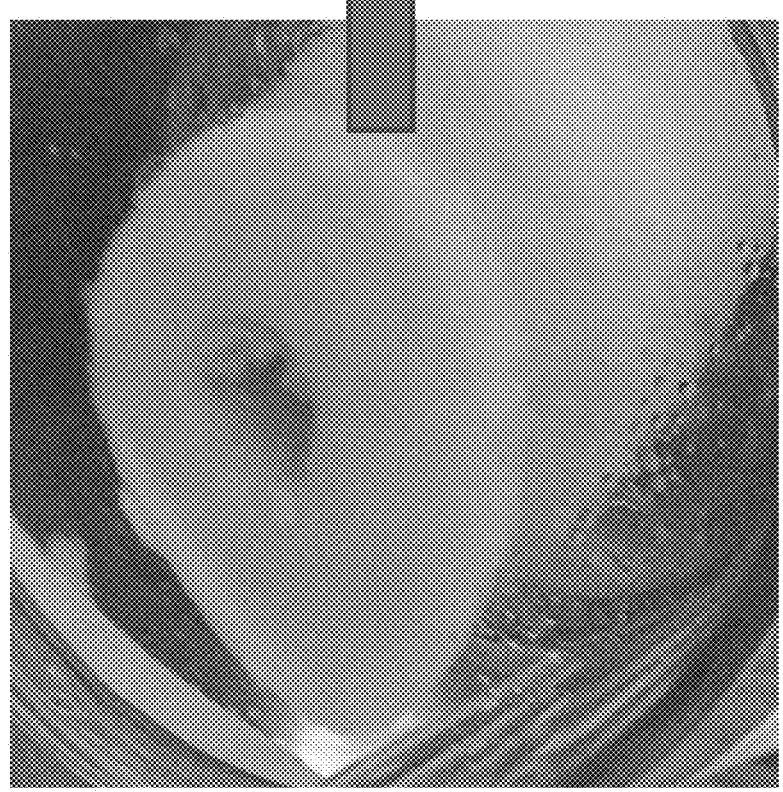
FIG. 7

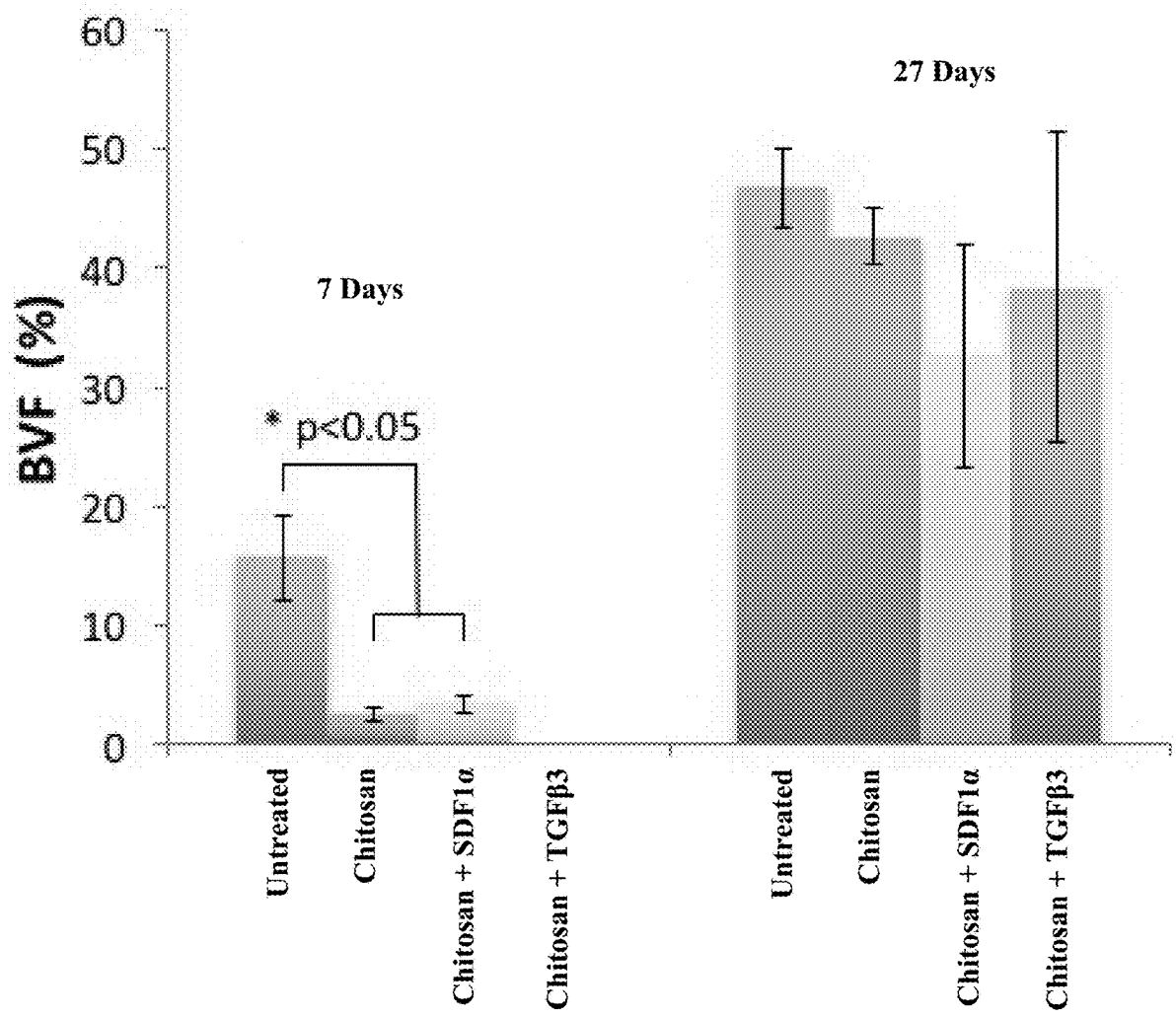

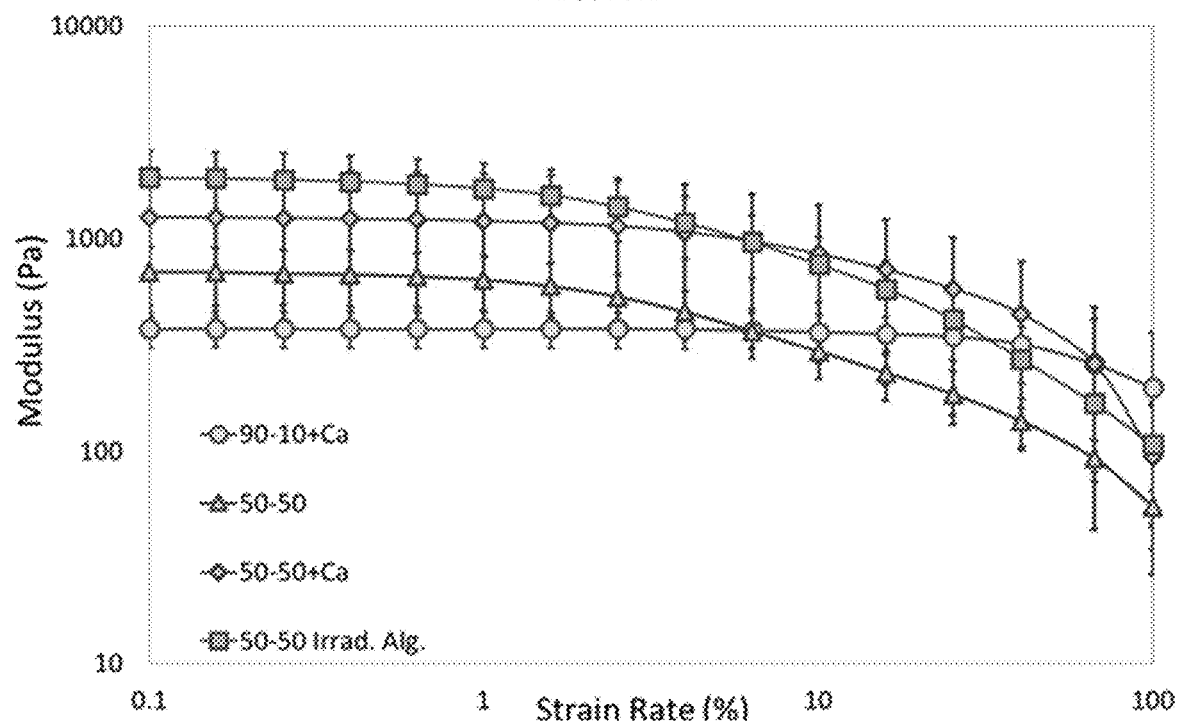
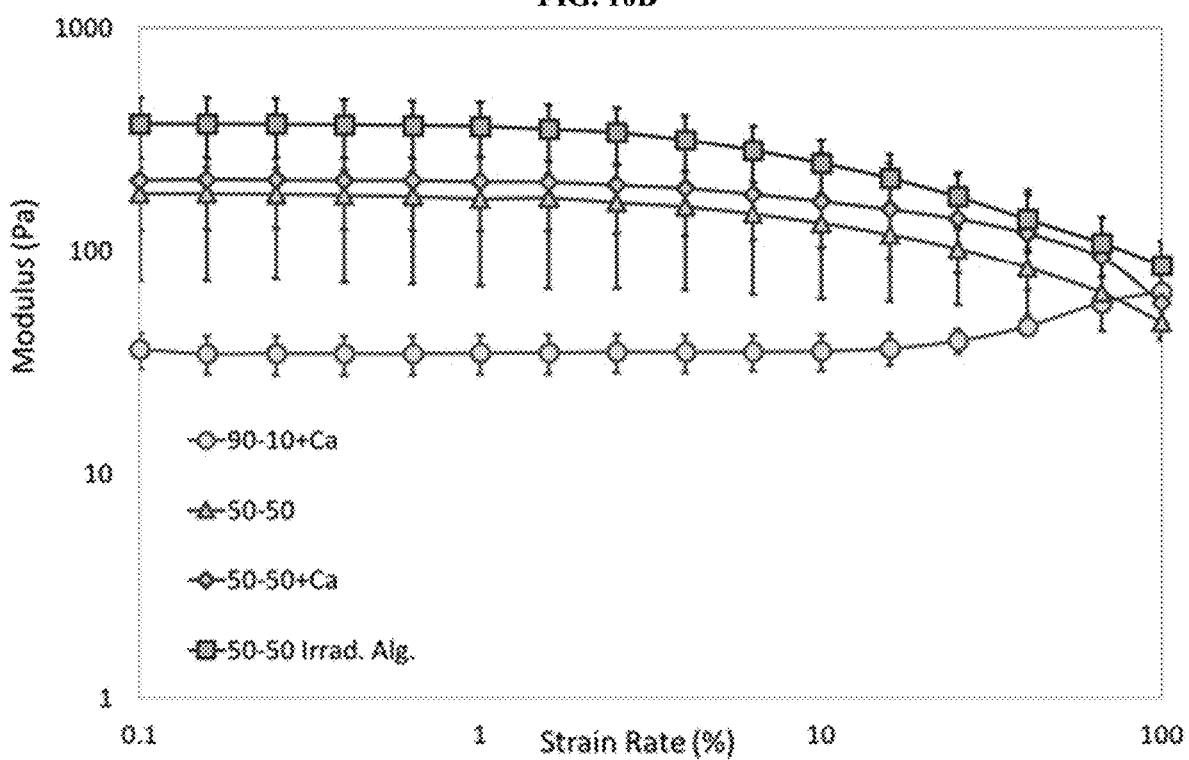

DMA Storage Modulus of Hydrogels at 1% Strain Rate (A) Irradiated Alginate PEC
(B) 7.5% Irradiated Alginate, 1% HA
(C) 7.5% Irradiated Alginate
(D) Irradiated Alginate PEC with HA DMA Storage Modulus of Hydrogels at 1% Strain Rate (A) 2% Alginate, 1% HA with CaSO4
(B) 2% Alginate with CaSO4
(C) Irradiated Alginate PEC
(D) Alginate PEC
(E) 15% Irradiated Alginate
(F) 7.5% Irradiated Alginate, 1% HA
(G) 7.5% Irradiated Alginate
(H) Irradiated Alginate PEC with CaSO4
(I) Irradiated Alginate PEC with HA
(J) Irradiated Alginate PEC with heat

HYDROGEL DRUG DELIVERY SYSTEMS FOR THE TREATMENT OF PEDIATRIC GROWTH PLATE INJURIES

CROSS-REFERENCE TO RELATED APPLICATIONS

The present application is a Continuation of U.S. patent application Ser. No. 16/762,860, filed May 8, 2020, which is a U.S. National Stage application filed under 35 U.S.C. 371 of PCT Application No. PCT/US2018/059460, filed Nov. 6, 2018, which claims priority under 35 U.S.C. § 119(e) to U.S. Provisional Application No. 62/583,047, filed Nov. 8, 2017, each of which is hereby incorporated by reference herein in its entirety for all purposes.

STATEMENT REGARDING FEDERALLY SPONSORED RESEARCH OR DEVELOPMENT

This invention was made with government support under grant number 1342222 awarded by the National Science Foundation and grant numbers R03 AR068087 and R21 AR071585 awarded by the National Institutes of Health. The government has certain rights in the invention.

BACKGROUND OF THE INVENTION

The growth plate or epiphyseal plate is found at the end of all long bones, and provides signals for long bones to lengthen as a child grows. It is made of cartilaginous tissue and is the most fragile structure in a child's developing bones, making it prone to injury. If the cartilage tissue in the growth plate is injured, bone tissue is deposited in the injured site, forming a "bony bar". This bony bar can stop bone growth completely, or can cause one side of the bone to grow more than the other, resulting in deformities. About 30% of all pediatric fractures affect the growth plate. Of those, 1-10% can lead to growth arrest or deformity. Current surgical methods to correct bone growth defects are invasive, prone to infections and have low success rates. The most common surgical approach is to remove the bony bar and insert a fat graft in its place. The fat is not as stiff as the bone, and may allow the remaining uninjured growth plate to maintain a normal bone growth pattern. Unfortunately, the fat graft often gets dislodged or dies due to lack of vascularization. Growth problems arising from growth plate injuries are devastating to the patient and family and can result in multiple surgeries, which increases the cost of treatment.

Thus, there is a need in the art for compositions and methods of treatment that will prevent bony bar formation and allow for the regeneration of the damaged growth plate, in order to prevent growth arrest and deformities. The present invention meets these needs.

BRIEF SUMMARY OF THE INVENTION

In one aspect, the invention provides a gel based composition comprising at least one hydrogel polymer material selected from the group consisting of chitosan and alginate; and at least one biological factor selected from the group consisting of anti-VEGF compounds, stem cell attracting factors, and transforming growth factor beta cytokines, wherein the gel is suitable for treatment of growth plate injuries.

In certain embodiments, the at least one biological factor is selected from the group consisting of SDF-1α, CCL25, TGF-β1, TGF-β3, ranibizumab, bevacizumab, lapatinib, sunitinib, sorafenib, axitinib, and pazopanib. In other embodiments, the at least one biological factor is a monoclonal antibody raised against VEGF.

In certain embodiments, the composition comprises a hydrogel polyelectrolyte complex (PEC) comprising chitosan and alginate, wherein the at least one biological factor is embedded within the hydrogel PEC. In other embodiments, the composition comprises a microgel comprising chitosan, wherein the at least one biological factor is embedded within the microgel. In yet other embodiments, the microgel is nested within a hydrogel comprising alginate. In yet other embodiments, the hydrogel comprising alginate comprises at least one biological factor. In yet other embodiments, the at least one biological factor embedded within the microgel is different from the at least one biological factor within the hydrogel. In yet other embodiments, the at least one biological factor within the hydrogel is released into a surrounding environment at a higher rate than the at least one biological factor within the microgel.

In certain embodiments, the chitosan is cross-linked with genipin.

In certain embodiments, the composition further comprises hyaluronic acid.

In another aspect, the invention provides a method of treating a growth plate injury in a subject, the method comprising administering to a subject in need thereof a therapeutically effective amount of a hydrogel composition of the invention.

In certain embodiments, the hydrogel composition is administered via injection. In other embodiments, the hydrogel composition is administered via direct injection to the growth plate injury. In yet other embodiments, before the administering, a bony bar is surgically removed from the growth plate injury in the subject.

In certain embodiments, the method prevents the growth of bony bars in the cartilage tissue at the site of the growth plate injury. In other embodiments, the method treats or prevents the arrest of bone growth at the site of growth plate injury. In yet other embodiments, the method treats or prevents bone deformities at the site of the growth plate injury.

In certain embodiments, the subject is a mammal. In other embodiments, the subject is a human. In yet other embodiments, the subject is an infant, toddler, child, juvenile, adolescent or young adult.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

*indicates a statistically significant difference of the control group from the experimental group with p<0.05.

Figure 3A:
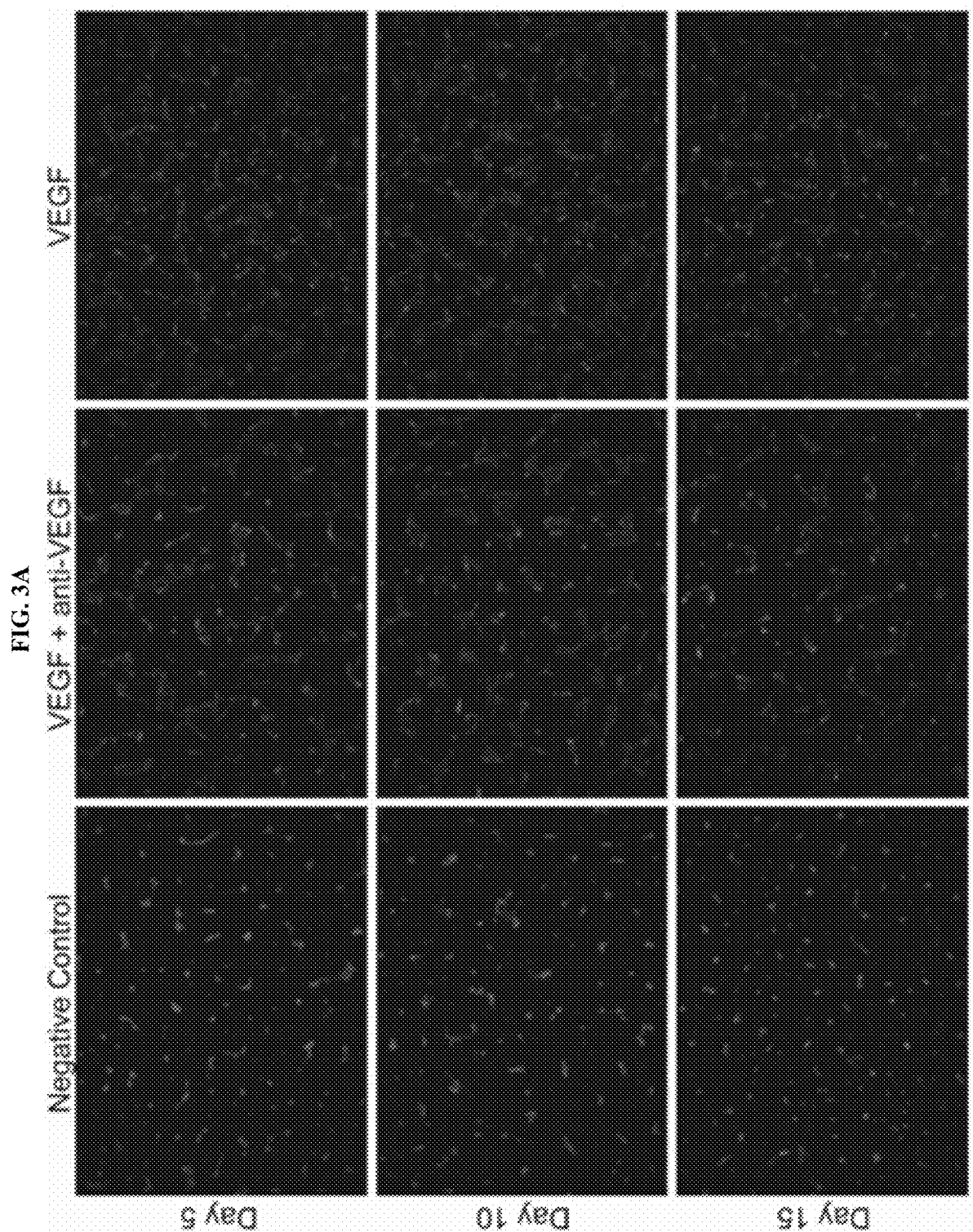
Figure 3B:
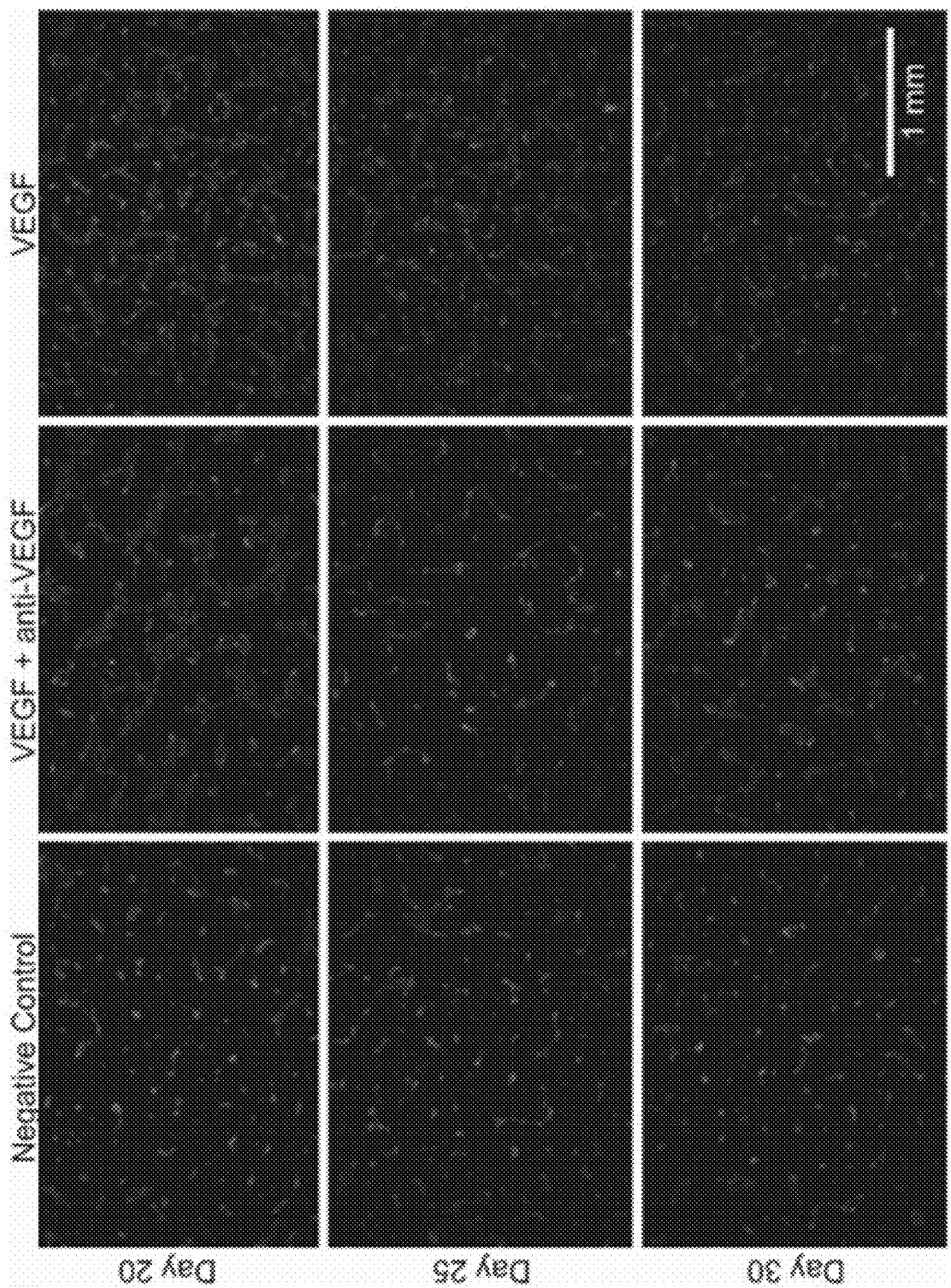

FIGS. 3A-3B are a series of images of HUVEC in vitro angiogenesis after 12 hours of exposure to medium that was conditioned by alginate-chitosan PECs over five day periods, during a 30 day release of anti-VEGF. The media for the negative control group (left images) without VEGF and without anti-VEGF, positive controls (right images) with VEGF but without anti-VEGF, and the experimental group (center images) with VEGF and with anti-VEGF released from the alginate-chitosan PECs used for conditioning.

Figure 4A:
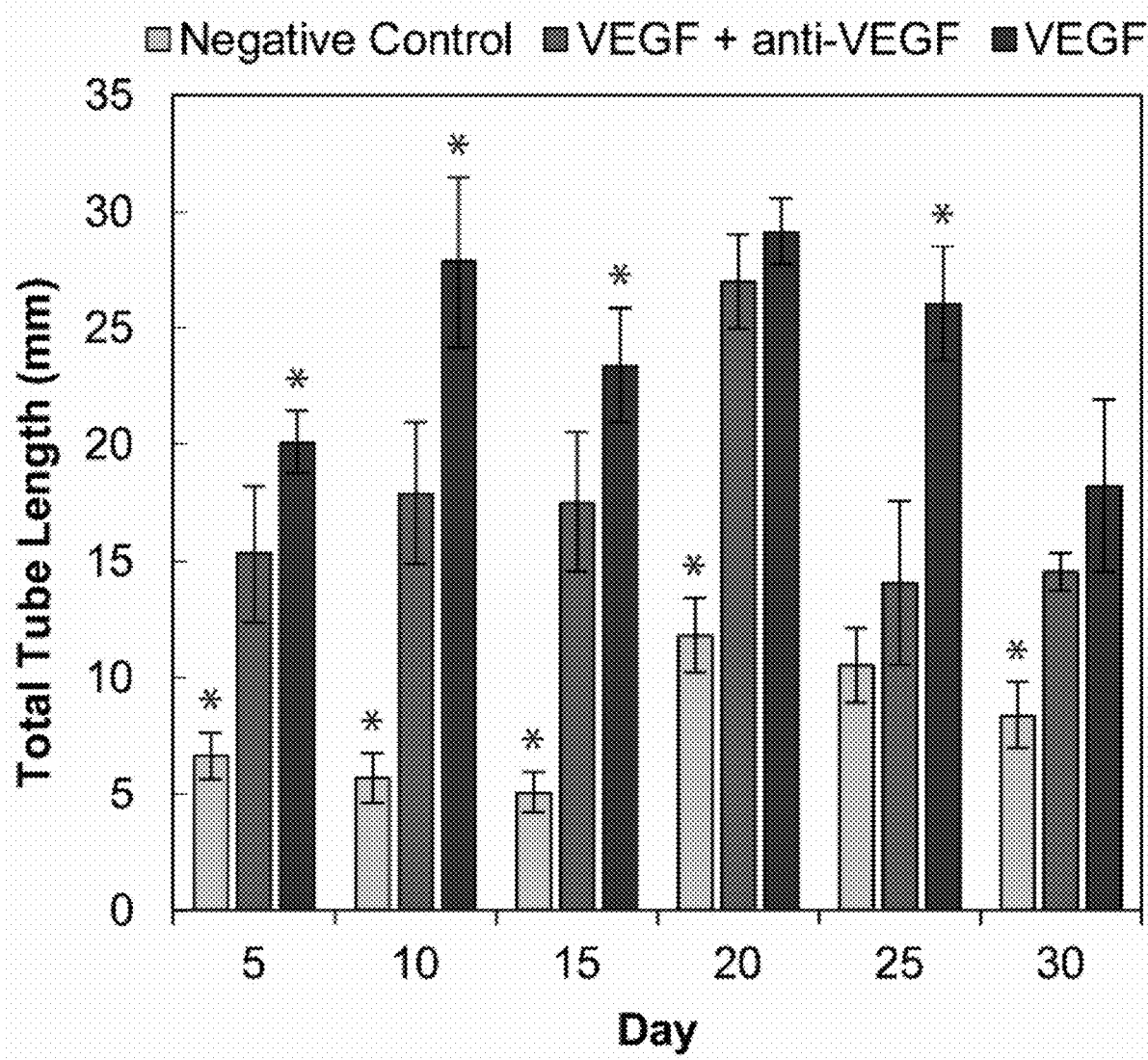

FIG. 4A is a graph of total tubule formation by HUVECs in cell culture medium conditioned by alginate-chitosan PECs every five days over a 30 day period. Light blue bars are the negative controls (medium without VEGF), dark blue are the positive controls (medium with 50 ng/mL VEGF), both of which were conditioned by blank PECs (without anti-VEGF antibody). The red bars show the experimental group (medium with 50 ng/mL VEGF) and were exposed to PECs loaded with anti-VEGF antibody. * indicates a statistically significant difference of the control group from the experiment group with p<0.05.

Figure 4B:
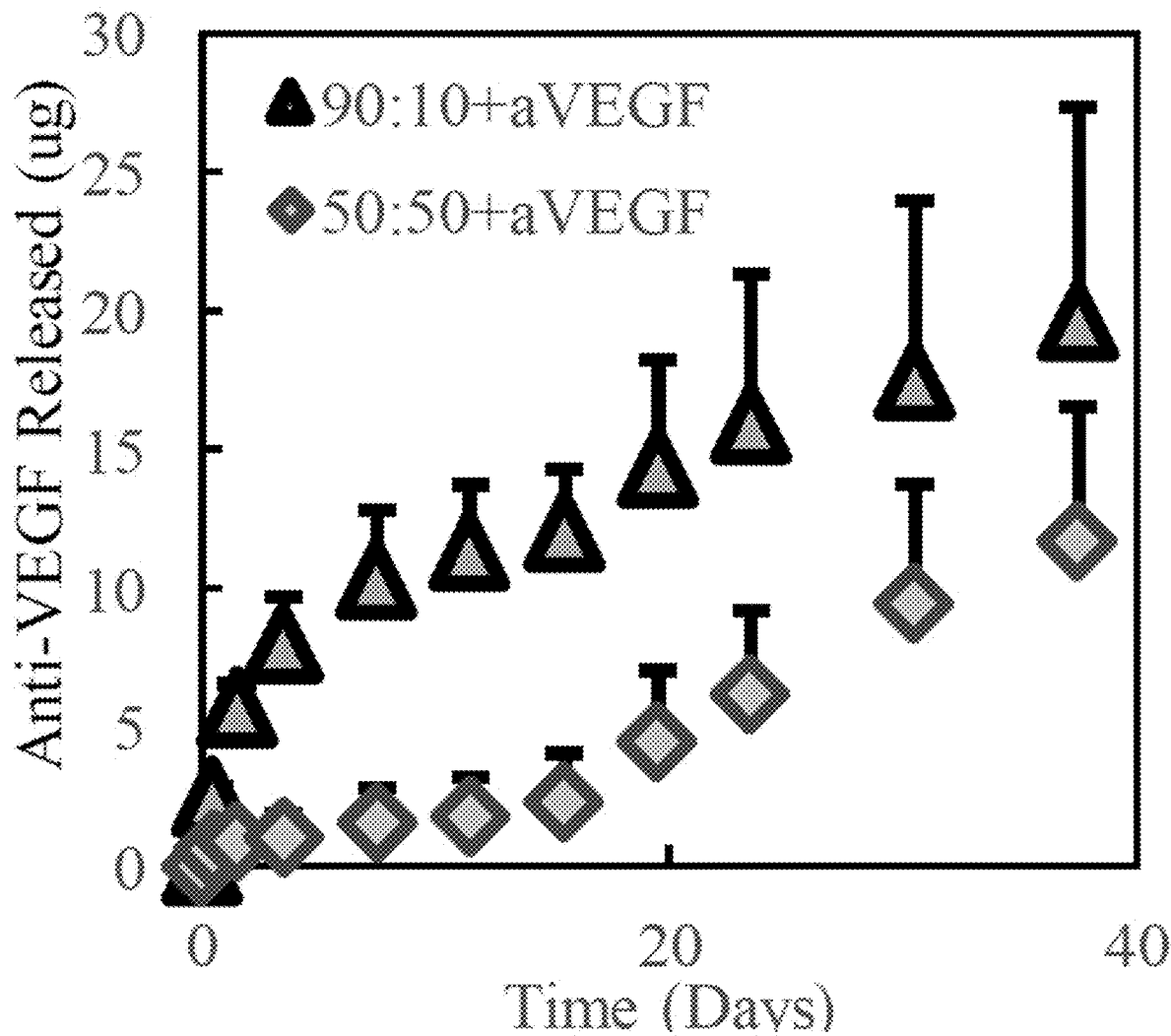

FIG. 4B is a graph showing the difference in anti-VEGF release between 50:50 and 90:10 formulations of alginate:chitosan compositions of the invention under in vitro release conditions.

Figure 5:
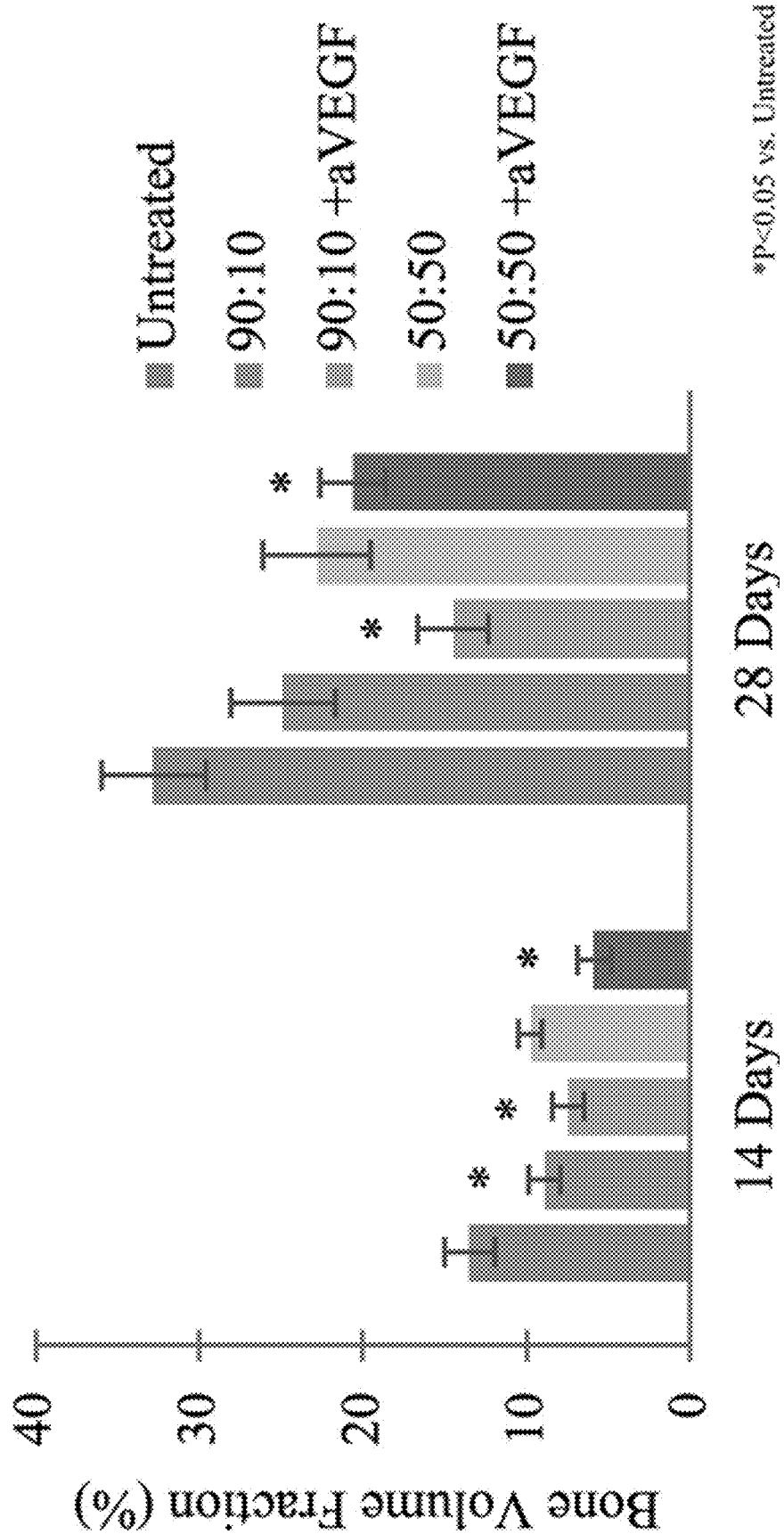

FIG. 5 is a graph of bone volume fraction in an injury site after administration of hydrogel compositions both with and without bevacizumab (anti-VEGF Ab). Mean+/−SEM; 14 days: n=4, 28 days: n=8; *P<0.05 vs. Untreated at same time point; #P<0.05 vs. same group at 14 days.

Figure 6A:
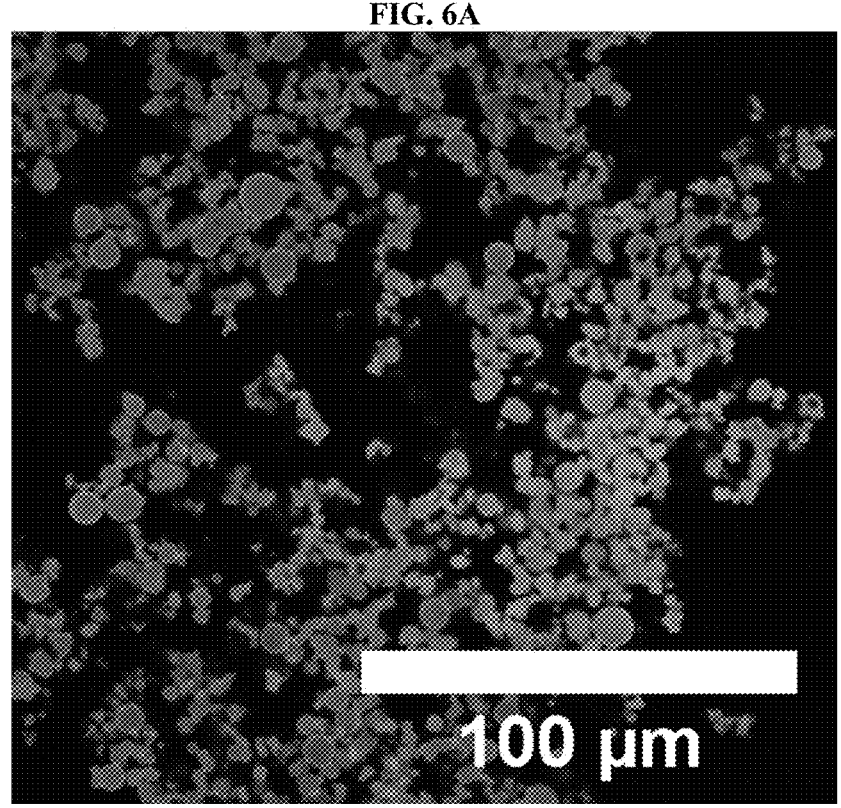
Figure 6B:
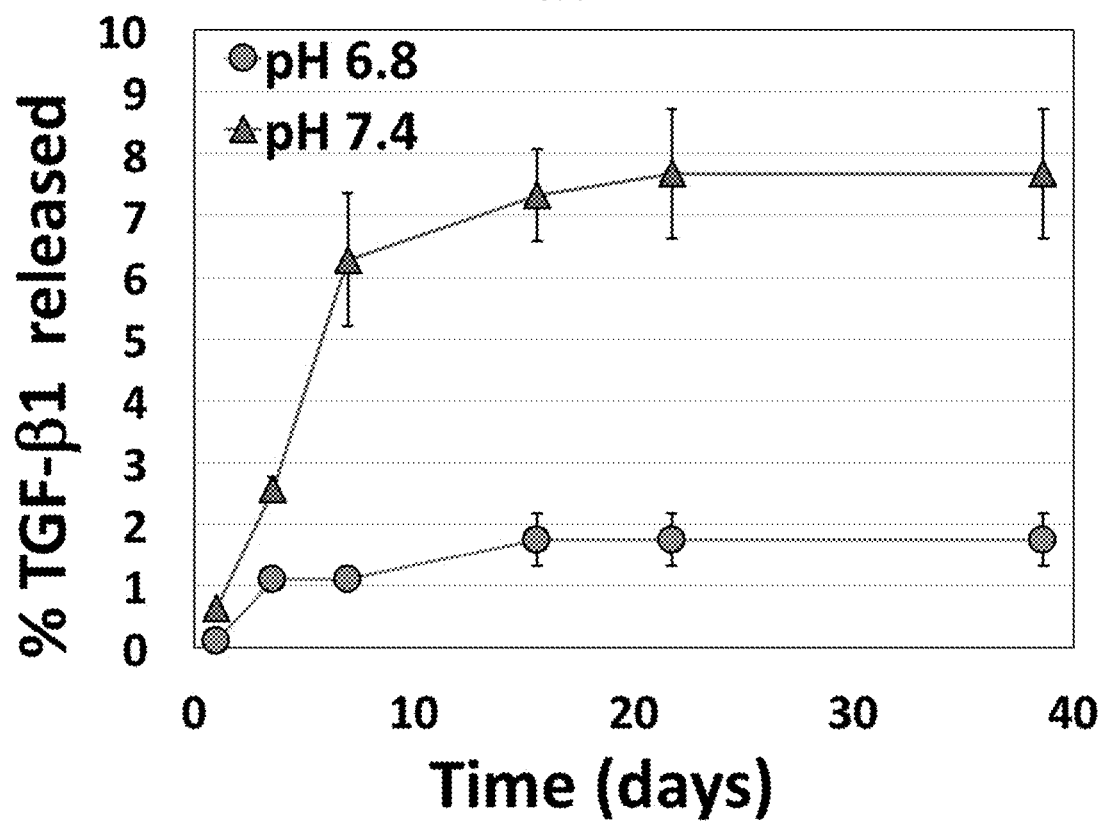

FIG. 6A is an image relating to certain embodiments of the invention. FIG. 6B is a graph tracking the release of TGF-β1 over time at both pH 6.8 and pH 7.4.

FIG. 7 is a set of images of bovine chondral explants before and after administration of microgels comprising chitosan and SDF-1α. Explants comprised a 4 mm diameter defect in 12 mm diameter osteochondral explant. All cartilage was removed down to the subchondral bone and the resulting void was filled with a microgel formulation.

Figure 8A:
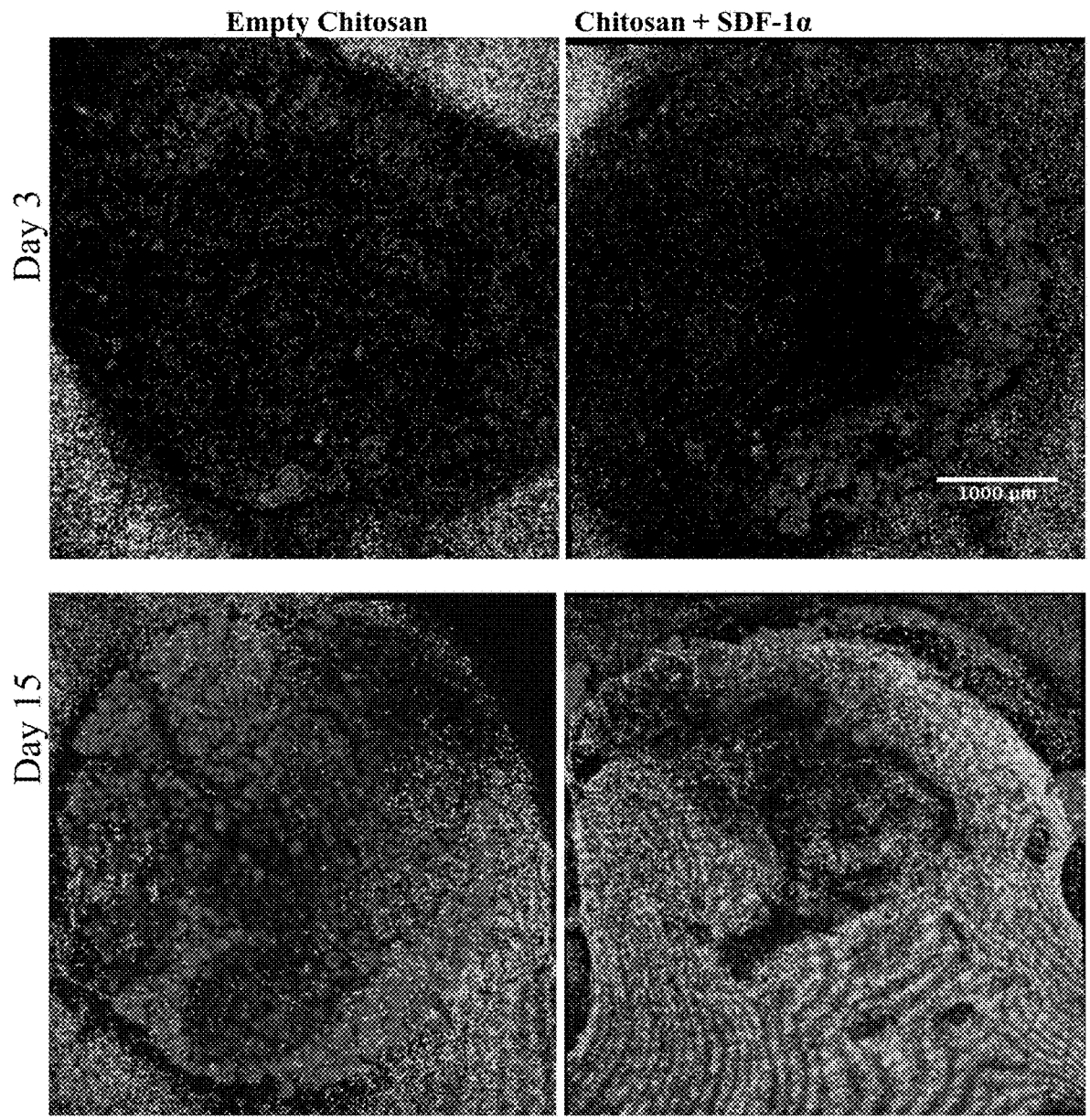
Figure 8B:
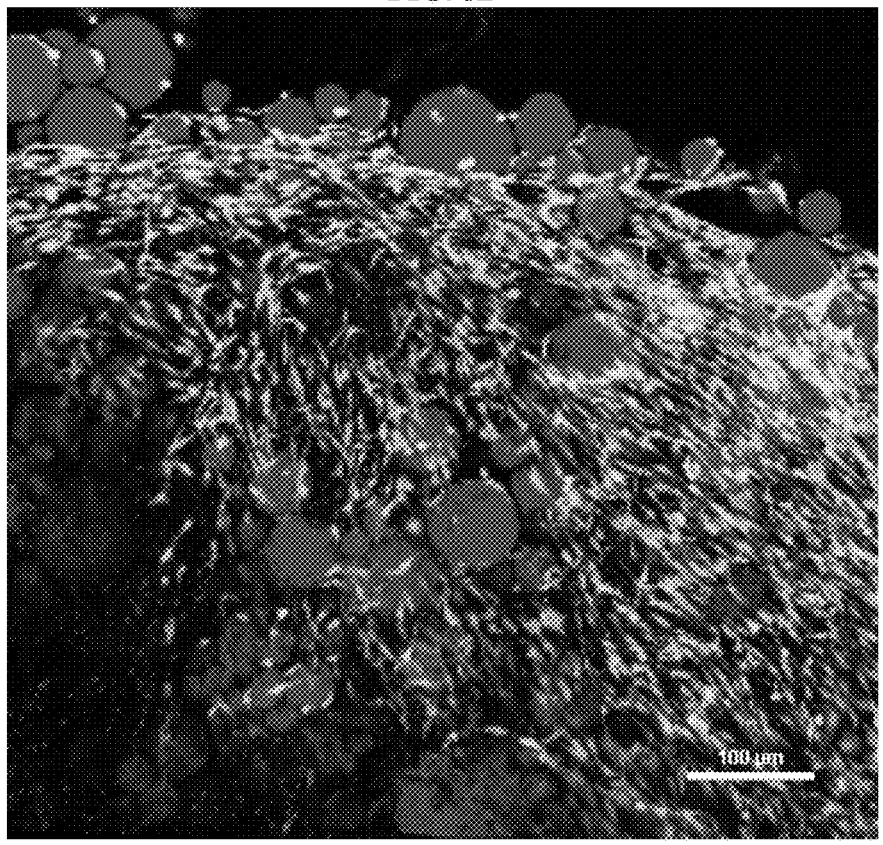
Figure 8C:
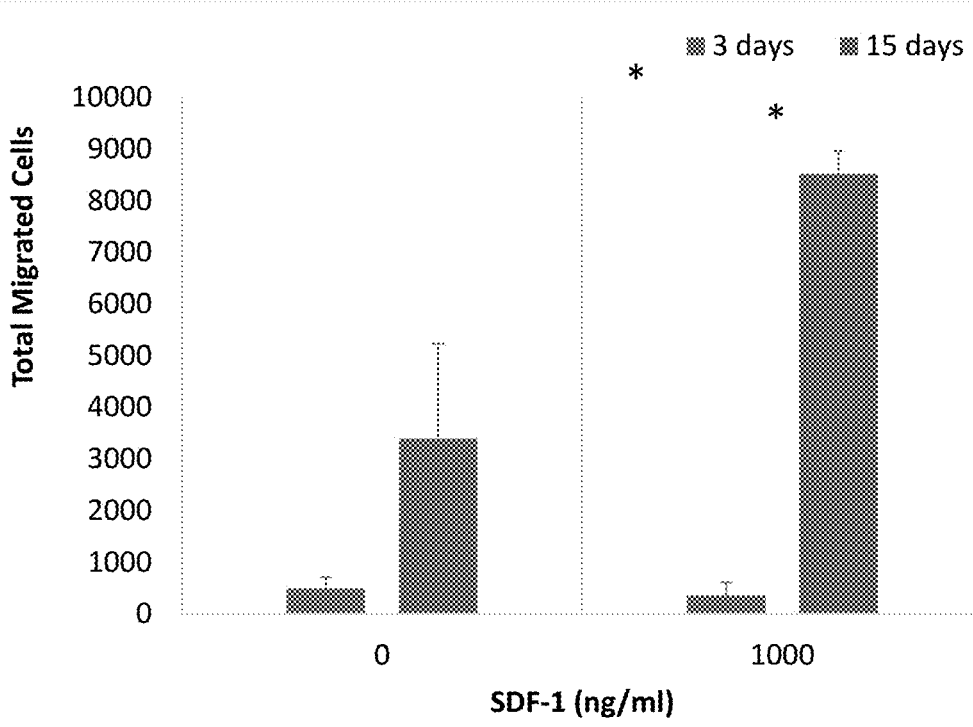

FIG. 8A is a set of images of ex vivo migration studies showing cell migration into SDF1α loaded chitosan microgels in the bovine chondral explants shown in FIG. 7. Red, chitosan; green, live cells. Dashed line circling defect. FIG. 8B is a detailed image of the chitosan microgel containing SDF-1α in FIG. 8A after 15 days. FIG. 8C is a graph reporting cell count data showing increased cell migration by day 15 in SDF-1α loaded chitosan microgels.

Figure 9B:
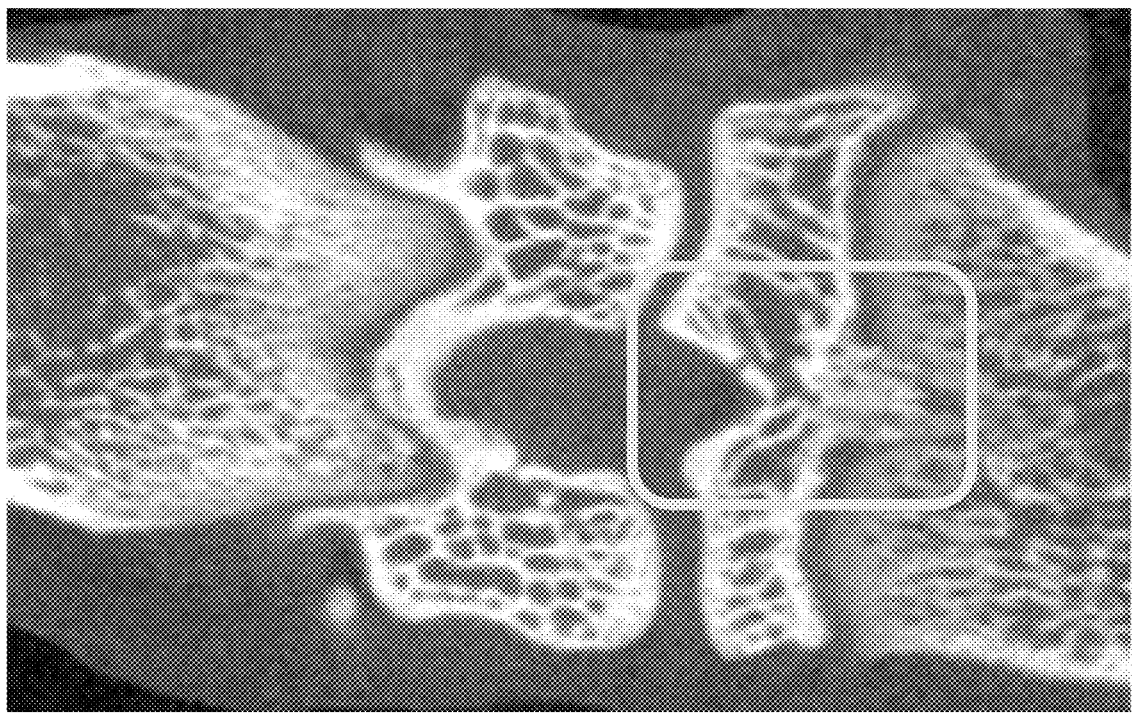
Figure 9A:
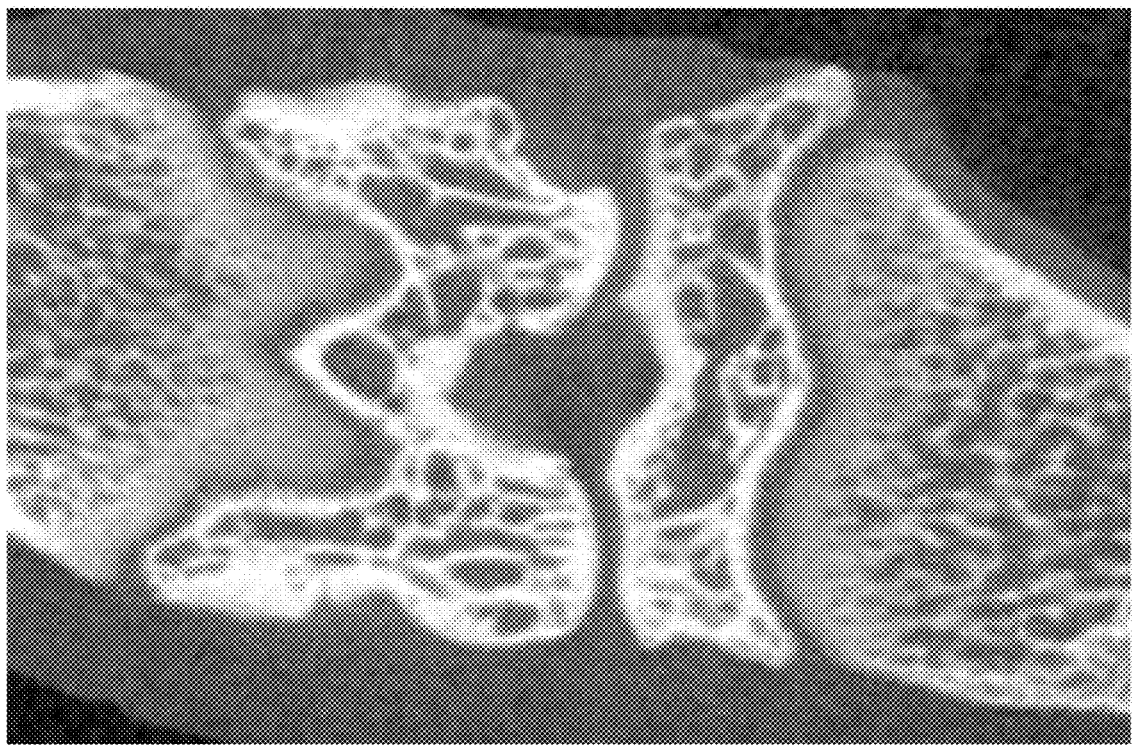
Figure 9D:
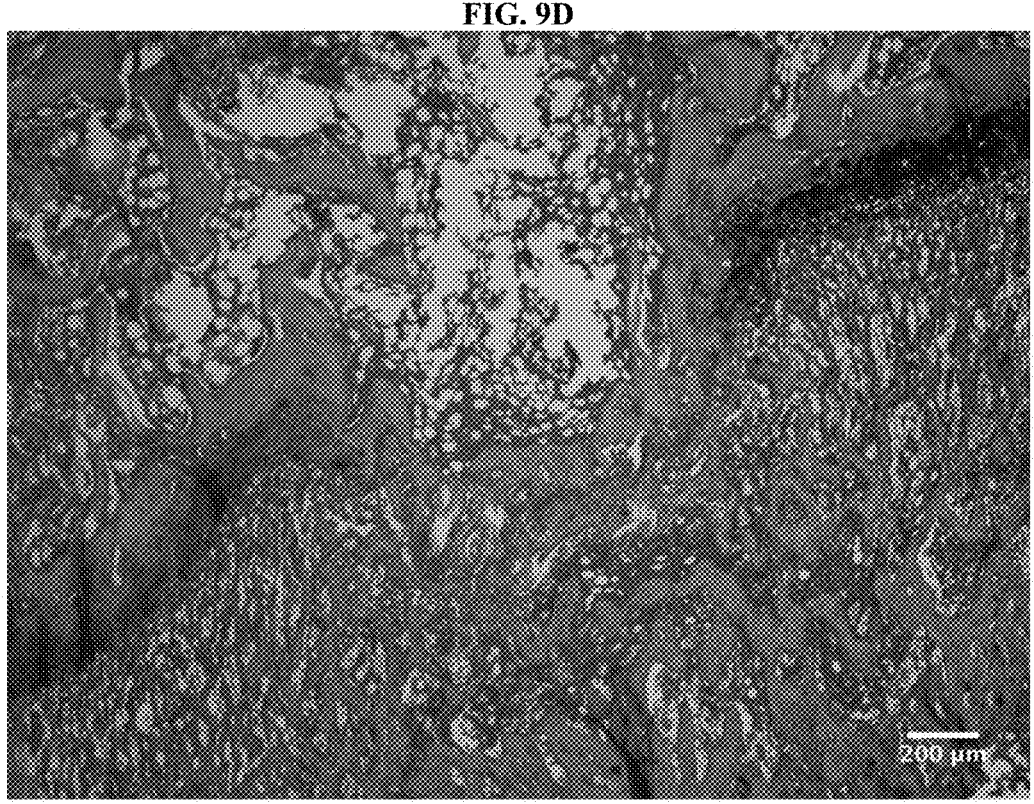
Figure 9E:
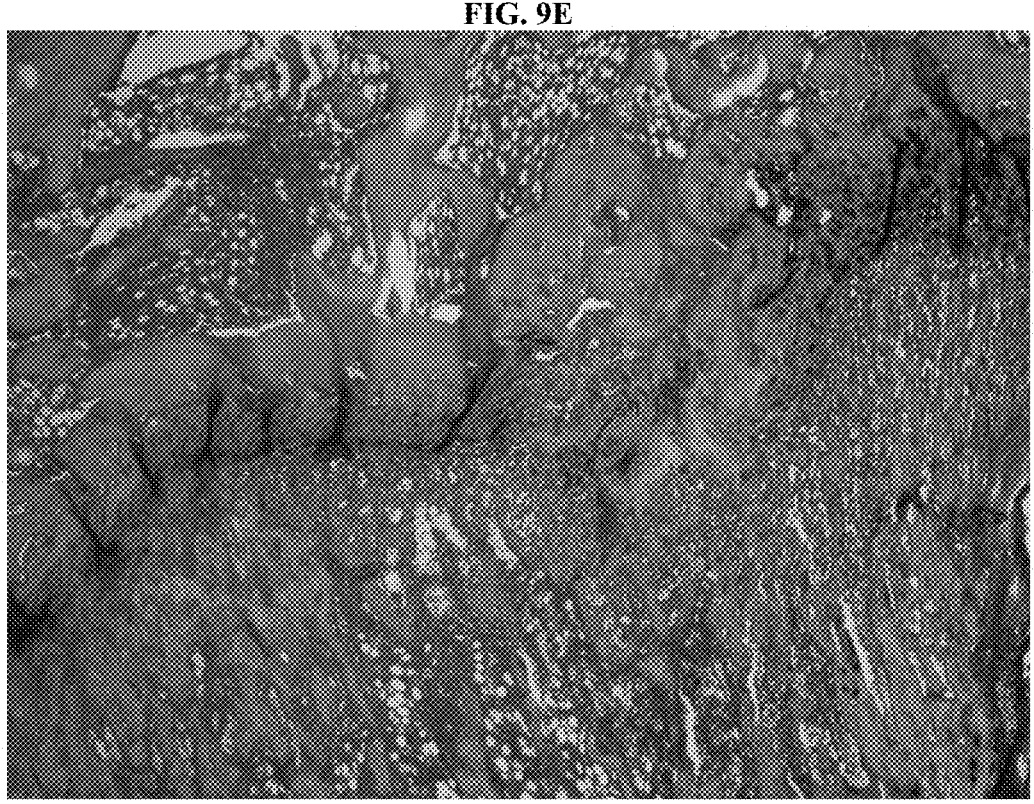
Figure 9F:
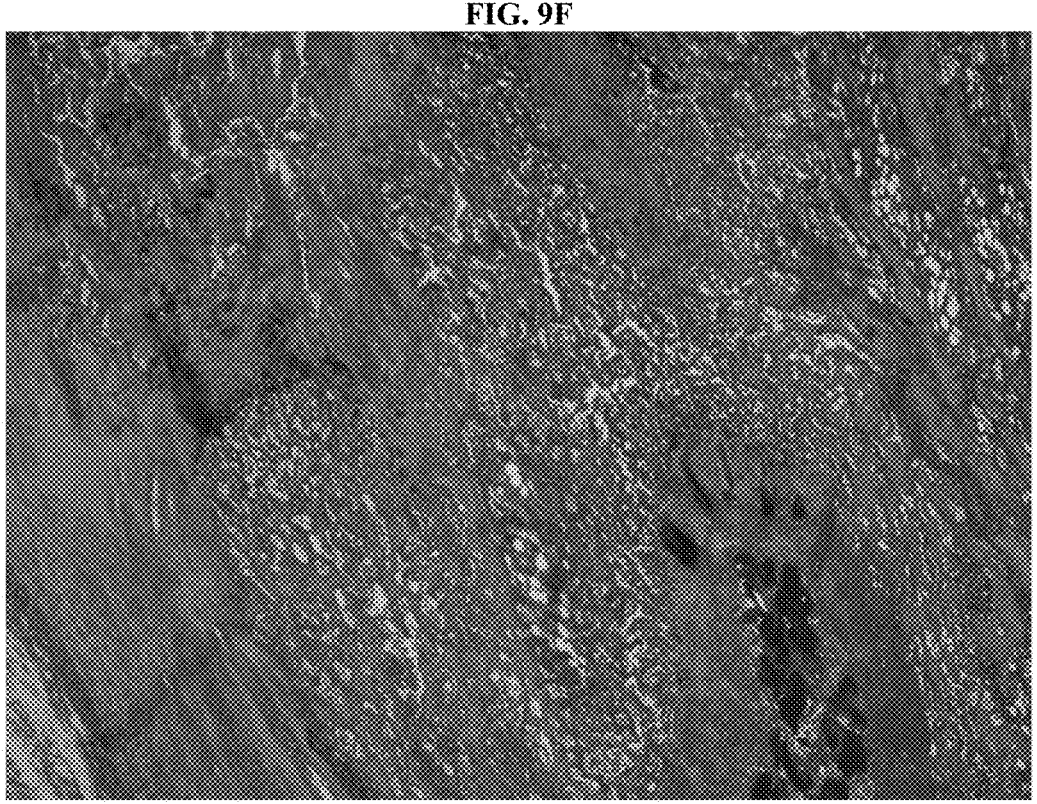
Figure 9G:
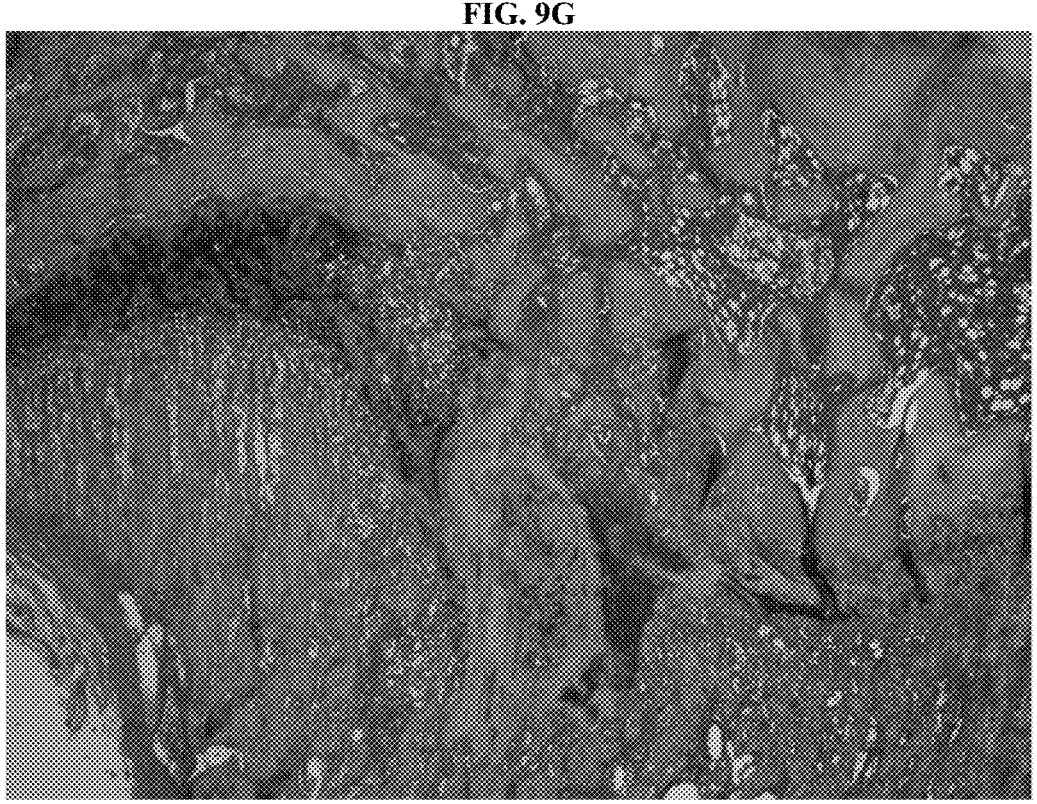

FIGS. 9A and 9B shown a rat knee joint before the introduction of a drill-hole defect in the growth plate (FIG. 9A) and 28 days after surgery with no treatment (FIG. 9B). FIG. 9C is a graph showing bone volume fraction (%) of repair tissue at the growth plate injury site as determined by microCT after treatment with various chitosan microgel formulations. FIGS. 9D-9G are representative histology images of the repair tissue 27 days after introduction of a drill-hole with no treatment (FIG. 9D), administration with empty chitosan microgel (FIG. 9E), administration of chitosan microgel containing SDF-1α (FIG. 9F) and administration of chitosan microgel containing TGF-β1 (FIG. 9G). Darker central bands are cartilage stained with Alcian Blue Hematoxylin.

FIGS. 10A-10B are graphs showing the results of rheology experiments conducted on the materials of the invention, showing the storage modulus in FIG. 10A and the loss modulus in FIG. 10B. The 50:50 irradiated alginate:chitosan PECs have the highest modulus at lower strain rates, followed by the 50:50+Ca then the 50:50 then the 90:10+Ca.

Figure 11A:
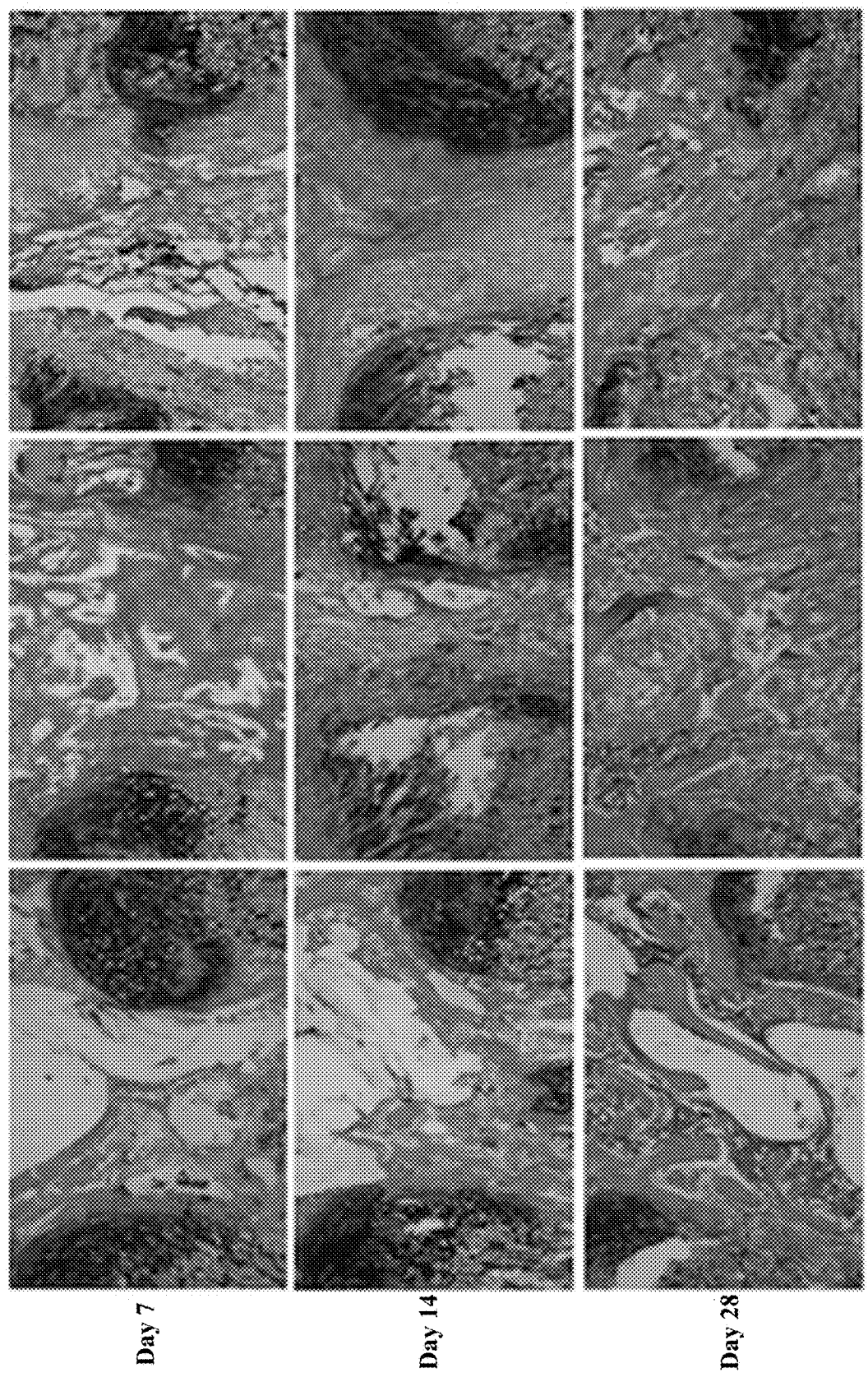

FIG. 11A is a set of histology images showing repair tissue and degradation at a physeal injury site following treatment with the alginate:chitosan microgels of the invention. At day 7, material was present at the injury site in all groups. The 90:10+Ca material was solid while both 50:50+Ca and 50:50−Ca had a spaghetti-like appearance; IA material had an amorphous shape with abundant cell infiltration. At day 14, 90:10+Ca 50:50+Ca and 50:50−Ca all remained within the injury site and had an appearance similar to the day 7 materials. The IA material was absent from the injury site at day 14. At day 28, the materials were all absent from the physeal injury site in all groups. (+Ca indicates the presence of added calcium, −Ca indicates the absence of added calcium)

Figure 11B:
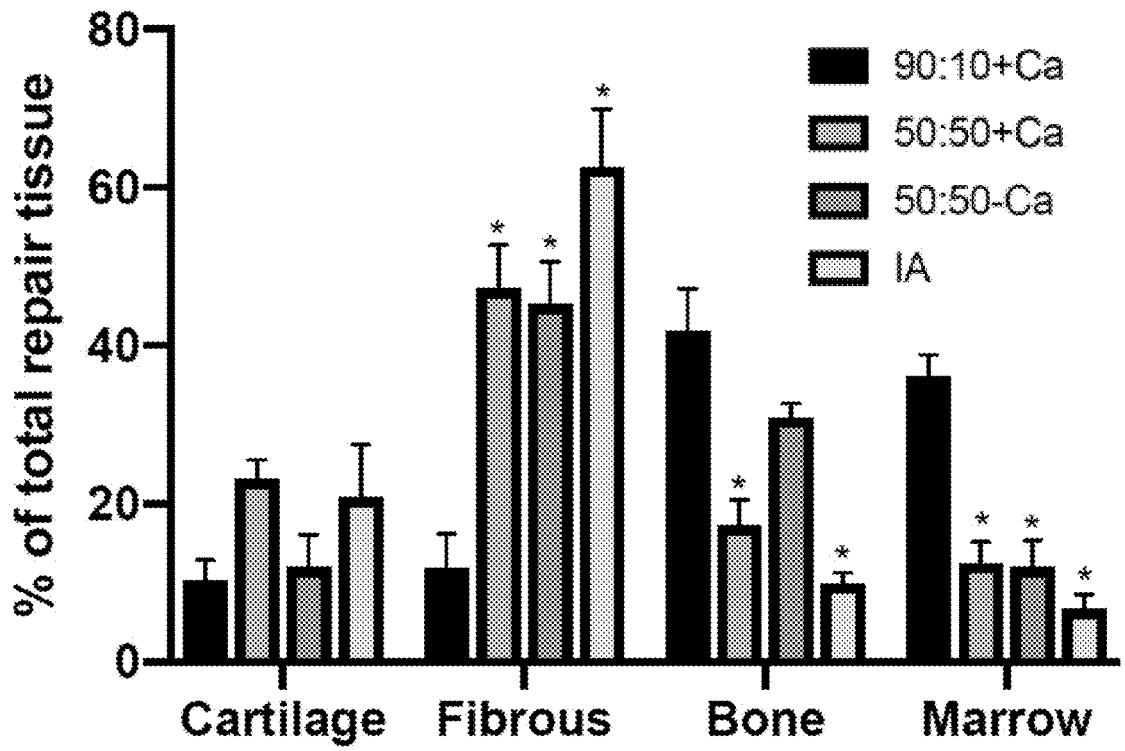
Figure 11C:
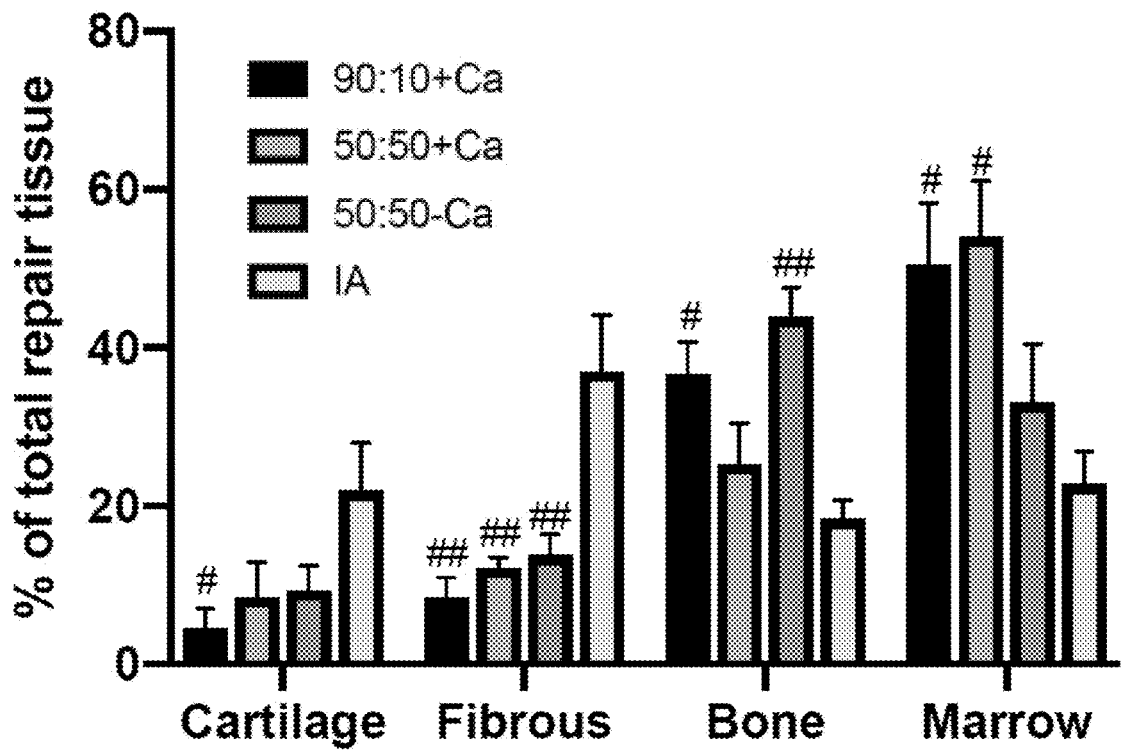

FIGS. 11B-11C are a set of graphs showing repair tissue proportions within the physeal injury site. Day 7 repair tissue was mostly fibrous (>80%) in all groups. At day 14 (FIG. 10B), 90:10+Ca had significantly less fibrous (p<0.002) and more bone marrow tissues (p<0.001) than the other groups. The IA material had more fibrous and less bone/marrow repair tissue than the other groups. By day 28 (FIG. 10C), groups treated with 90:10+Ca, 50:50+Ca and 50:50−Ca developed mature bony bars at the growth plate injury site. IA treated groups had more cartilage (p=0.05 vs. 90:10+Ca only) and fibrous tissues (p<0.005 vs. all groups), and less bone (p<0.05 vs. 90:10+Ca and 50:50−Ca) and marrow tissues (p<0.05 vs. 90:10+Ca and 50:50−Ca) than the other groups. Data is represented as mean+/−SEM. *P<0.01 vs. 90:10+Ca within the same tissue type. #P<0.05 vs. IA within the same tissue type. ##P<0.01 vs. IA within the same tissue type.

Figure 12:
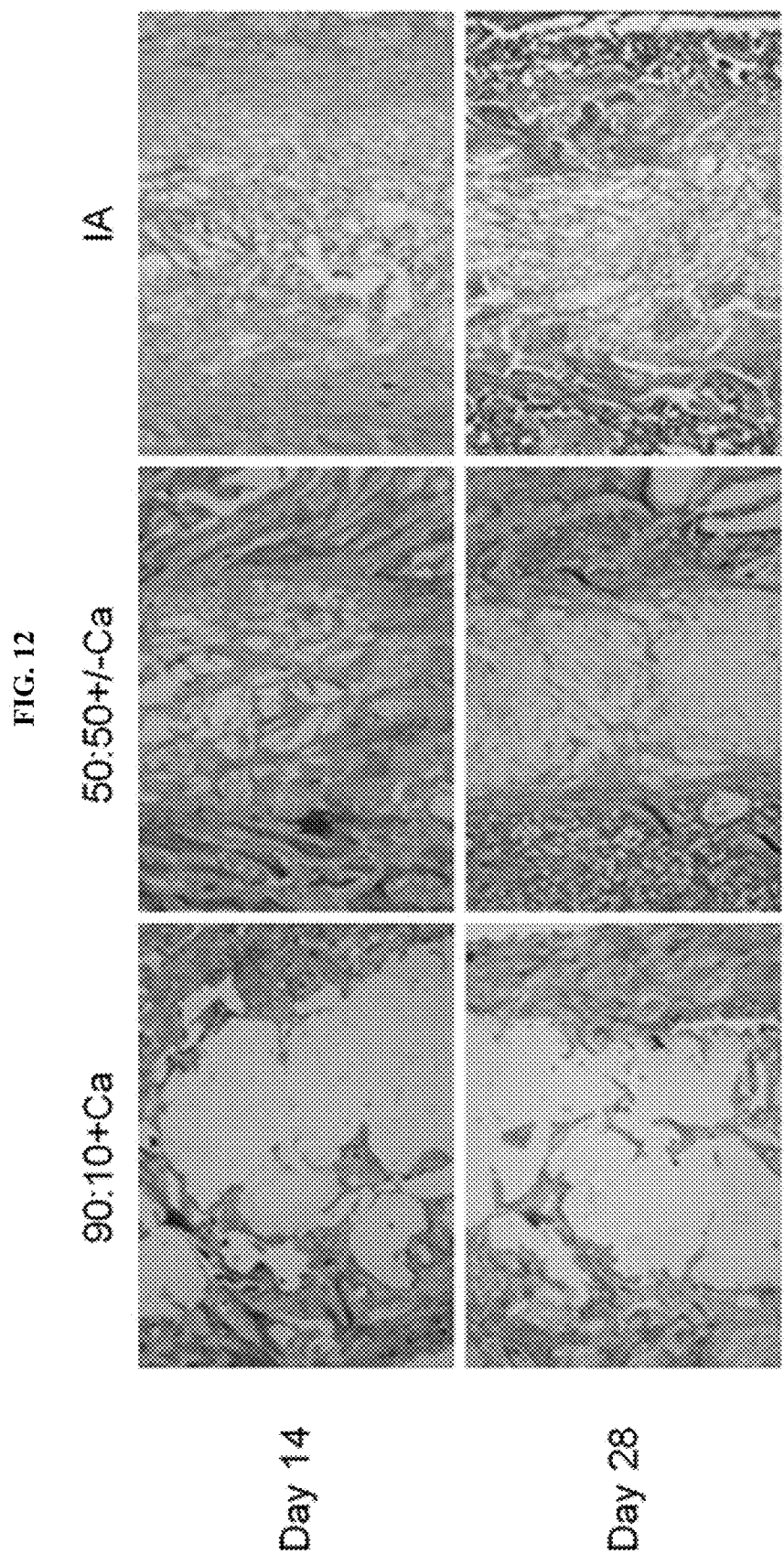

FIG. 12 is a set of histology images at the drill track site showing differential degradation of hydrogels with various formulations. The 90:10+Ca material remained solid within the drill track at all time points, showing little degradation over time. The 50:50+/−Ca groups remained intact within the drill track, but showed degradation over time. These materials allowed for cell migration as seen by cellular infiltrate. IA degrades rapidly within the drill track over time allowing for abundant cell infiltration.

Figure 13:
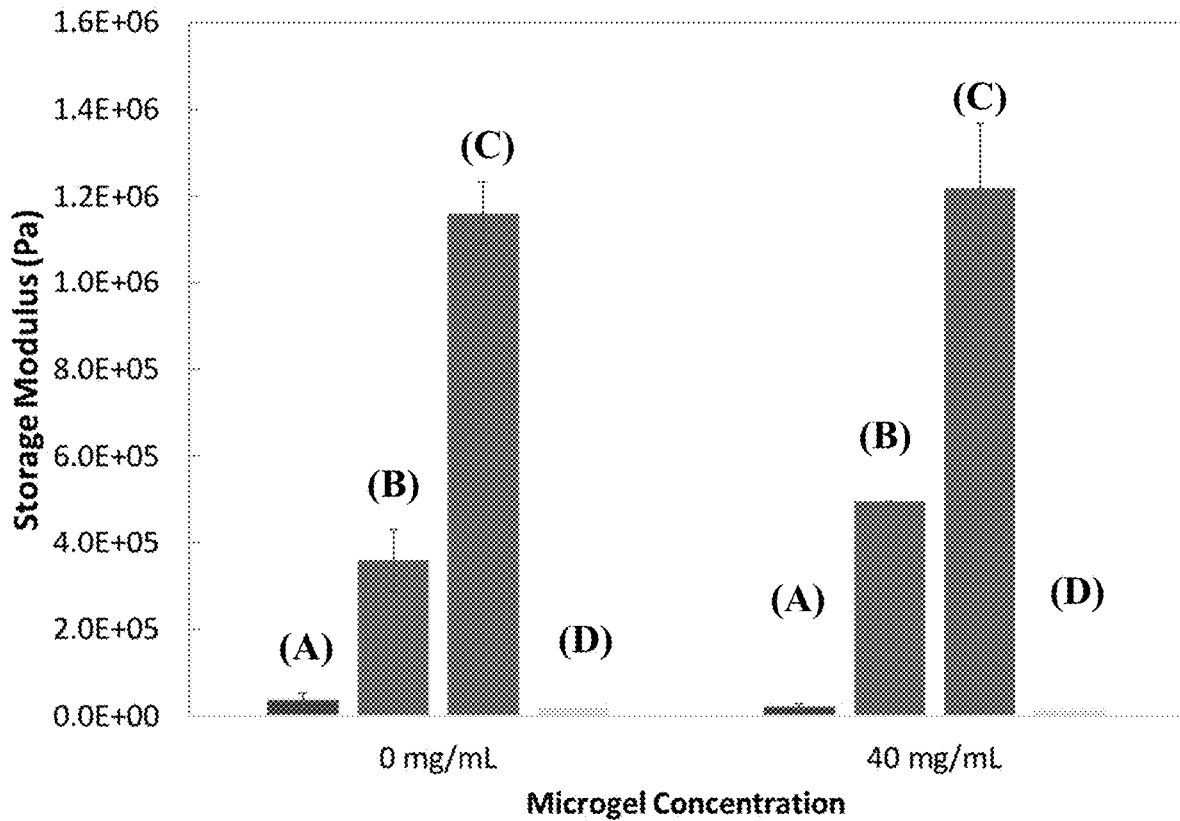
Figure 14:
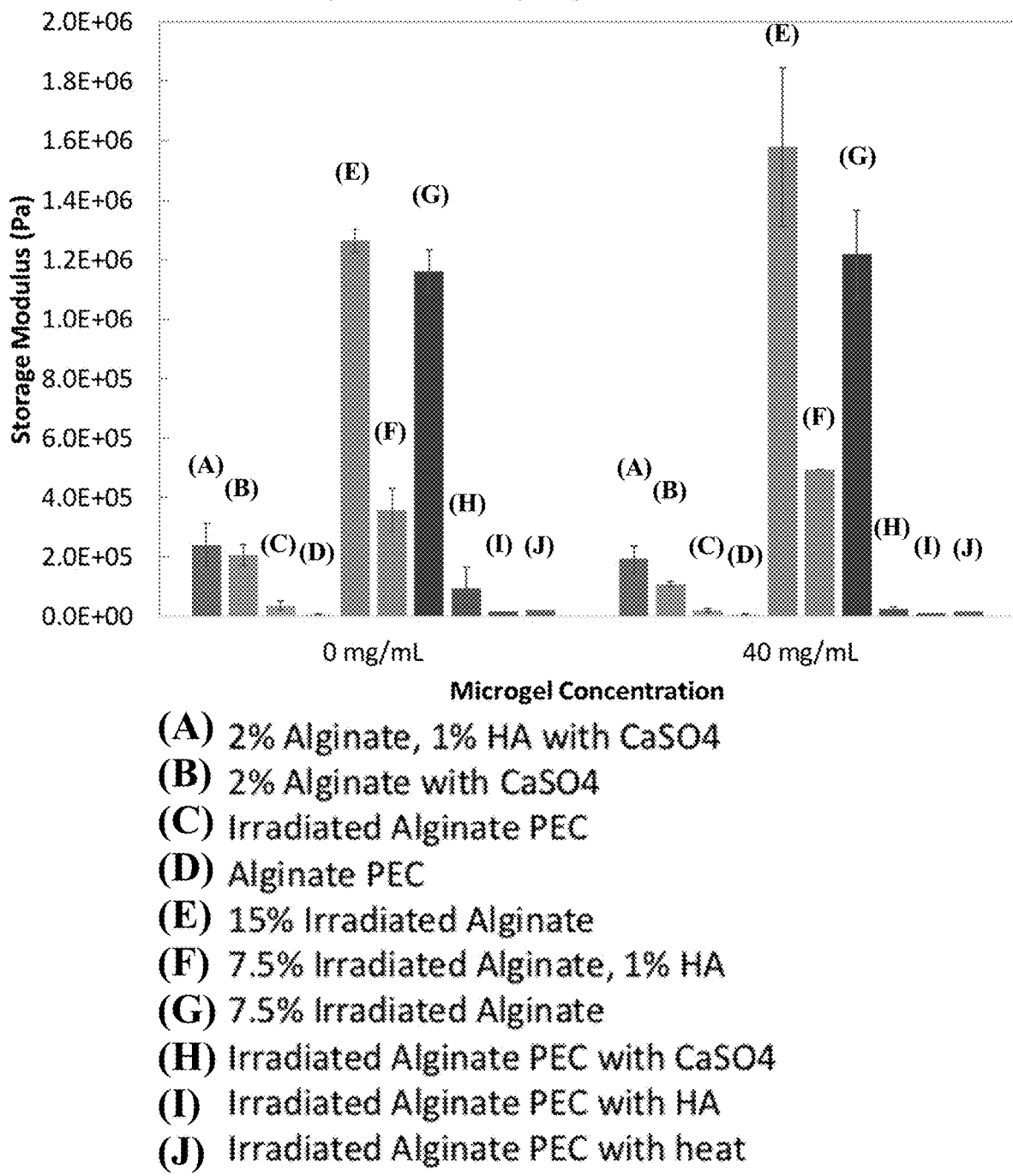

FIGS. 13 and 14 are graphs reporting the storage modulus at 1% strain rate of various gel formulations of the invention.

DETAILED DESCRIPTION OF THE INVENTION

The present invention relates to the unexpected discovery of compositions and methods for the treatment of growth plate defects. In certain embodiments, the methods prevent the growth of "bony bars" at the site of growth plate injury, thereby preventing growth arrest and/or deformity.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in pharmacology and tissue engineering are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein "alginate" is meant to be a polysaccharide comprising copolymer chains of mannuronic acid and guluronic acid, extracted from brown algae, as well as physically, chemically and/or enzymatically derivatized forms thereof.

As used herein, "Anti-VEGF antibody" or "Anti-VEGF ab" refers to VEGF165 monoclonal mouse antibody.

As used herein, the term "bony bar" or "physeal bar" is a premature physeal arrest, often resulting from injury or infection to an unfused physis. The bony bar consists of a bony bridge that crosses the growth plate and can result in growth abnormalities and deformities.

As used herein "chitosan" is a linear polysaccharide composed of randomly distributed β-(1→4)-linked D-glucosamine (deacetylated unit) and N-acetyl-D-glucosamine (acetylated unit).

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

As used herein "crosslinking" is meant to be a process of creating a bond that links one polymer chain to another.

As used herein "crosslinking agent" or "crosslinking source" is meant to be an agent that is capable of forming a chemical or ionic links between molecules. Nonlimiting examples of crosslinking agents or sources include calcium chloride; ammonium persulfate (APS) and tetramethylethylenediamine (TEMED), glutaraldehyde, epoxides, oxidized dextran, p-azidobenzoyl hydrazide, N-[α.-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS), visible light irradiation, ultraviolet irradiation, and combinations thereof.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" will be used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

As used herein, the term "growth plate" refers to the epiphyseal plate or the hyaline cartilage plate in the metaphysis at each end of a long bone. The growth plate is the portion of the bone where new bone growth takes place, thereby elongating the bone.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions.

The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "effective amount" or "therapeutically effective amount" of a compound is that amount of compound that is sufficient to provide a beneficial effect to the subject to which the compound is administered.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: BM-MSCs, bone marrow mesenchymal stem cells; CS, chitosan; diH2O, deionized water; GP, genipin; HUVECs, human umbilical vein endothelial cells; I-CS, irradiated chitosan; IgG, immunoglobulin G; MSC, mesenchymal stem cell; PEC, polyelectrolyte complex; RGD, arginine-glycine-aspartic acid; VEGF, vascular endothelial growth factor

Compositions

The present invention provides gel based compositions for the treatment of growth plate injuries. In certain embodiments, the composition of the invention comprises: at least one hydrogel polymer material selected from the group consisting of chitosan and alginate; and at least one biological factor selected from the group consisting of anti-VEGF compounds, stem cell attracting factors and transforming growth factor beta cytokines.

In certain embodiments, the at least one biological factor is selected from the group consisting of SDF-1α, CCL25, TGF-β1, TGF-β3, ranibizumab, bevacizumab, lapatinib, sunitinib, sorafenib, axitinib, and pazopanib. In other embodiments, the at least one biological factor is a monoclonal antibody raised against VEGF.

In certain embodiments, the composition comprises a hydrogel polyelectrolyte complex (PEC) comprising chitosan and alginate; further comprising at least one biological factor embedded within the hydrogel PEC. In certain embodiments, the hydrogel PEC comprises chitosan and alginate in a 50/50 ratio. In other embodiments, the hydrogel PEC comprise chitosan and alginate in a 10/90 ratio.

In certain embodiments, the composition comprises a microgel comprising chitosan comprising at least one biological factor embedded within the microgel. In other embodiments, the microgel is nested within a hydrogel comprising alginate. In yet other embodiments, the hydrogel comprising alginate comprises at least one biological factor. In yet other embodiments, the at least one biological factor embedded within the microgel is different from the at least one biological factor within the hydrogel. In certain embodiments, the biological factor within the hydrogel can be released into a surrounding environment more quickly while the biological factor within the microgel can be released more slowly.

In certain embodiments, the composition comprises at least one cross-linking agent. In other embodiments, the cross-linking agent is selected from the group consisting of genipin.

In certain embodiments, the composition further comprises hyaluronic acid. In other embodiments, the hydrogel polyelectrolyte complex (PEC) further comprises hyaluronic acid. In yet other embodiments, the amount of hyaluronic acid in the composition can be modified in order to modulate at least one property of the gel selected from the group consisting of stiffness, stability, porosity, and cell interaction.

In certain embodiments, the gel compositions of the invention are stable in an in vivo growth plate injury environment for a period of about less than one day to about 21 days. In other embodiments, the gel compositions of the invention are stable in an in vivo growth plate injury environment for a period of about 1 day to about 14 days. In yet other embodiments, the gel compositions of the invention degrade within an in vivo growth plate injury environment after more than 28 days.

Methods

The invention provides a method of treating growth plate injuries in a subject. In certain embodiments, the method prevents the growth of bony bars in cartilage tissue at the site of growth plate injury. In other embodiments, the method treats or prevents the arrest of bone growth at the site of growth plate injury. In yet other embodiments, the method treats or prevents bone deformities at the site of growth plate injury.

In certain embodiments, the method comprises administering to a subject in need thereof a therapeutically effective amount of a hydrogel composition of the invention described elsewhere herein.

In certain embodiments, the hydrogel composition is administered via injection. In other embodiments, the hydrogel compositions is administered directly to the growth plate injury.

In certain embodiments, the method comprises first surgically removing a bony bar from the growth plate injury in the subject and then administering to the subject a therapeutically effective amount of the hydrogel composition.

In certain embodiments, the subject is a mammal. In other embodiments, the subject is a human. In yet other embodiments, the subject is an infant, toddler, child, juvenile, adolescent or young adult. In yet other embodiments, the subject has active growth plates and has not undergone epiphyseal closure.

Combination and Concurrent Therapies

In one embodiment, the compounds of the invention are useful in the methods of present invention when used concurrently with at least one additional compound useful for preventing and/or treating diseases and/or disorders contemplated herein.

In one embodiment, the compounds of the invention are useful in the methods of present invention in combination with at least one additional compound useful for preventing and/or treating diseases and/or disorders contemplated herein.

These additional compounds may comprise compounds of the present invention or other compounds, such as commercially available compounds, known to treat, prevent, or reduce the symptoms of diseases and/or disorders contemplated herein. In certain embodiments, the combination of at least one compound of the invention or a salt thereof, and at least one additional compound useful for preventing and/or treating diseases and/or disorders contemplated herein, has additive, complementary or synergistic effects in the prevention and/or treatment of diseases and/or disorders contemplated herein.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the compound and the agent are physically mixed in the composition. In another embodiment, the compound and the agent are physically separated in the composition.

A synergistic effect may be calculated, for example, using suitable methods such as, for example, the Sigmoid-Emax equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Protanal LF 20/40 alginate and the chitosan salts Protasan UP CL 213 (chlorine counterion 13%, 83% deacetylated, 101 mPa s apparent viscosity, batch no. BP-0805-04) and Protasan UPG 213 (glutamate counterion 40%, 85% deacetylated, 36 mPas apparent viscosity, batch no. FP-308-03) were from FMC BioPolymer (Philadelphia, PA). The peptide glycine(×4)-arginine-glycine-aspartic acid-serine-proline (G4RGDSP) was purchased from Mimotopes (Victoria, Australia). G4RGDSP was covalently coupled to the alginate as has been previously described (Rowley et al., 1999); specifically 5 g of alginate was dissolved in 500 mL of MES buffer (0.1 M 2-(N-morpholino)ethanesulfonic acid (Sigma-Aldrich, St. Louis, MO) at pH 6.5 with 0.3 M sodium chloride) and then 62.5 mg of G4RGDSP peptide was added along with 137 mg N-hydroxysulfosuccinimide (sulfo-NHS; Thermo Scientific; Waltham, MA) and 242.1 mg 1-ethyl-3-(dimethylaminopropyl) carbodiimide (EDC; ProteoChem; Hurricane, UT). The reaction proceeded for 20 h at room temperature with stirring before quenching with 90 mg of hydroxylamine hydrochloride (Sigma-Aldrich). Both the unmodified alginate and the RGD-modified alginate (RGD-alginate) were dialyzed in regenerated cellulose tubing with 3500 MWCO (Fisherbrand) for 4 days against purified water, and then subjected to activated charcoal treatment (0.5 g per 100 mL of alginate solution). The alginate solutions and chitosan solutions were all sterilized through 0.22-μm filters, frozen, and lyophilized prior to use. Purified Immunoglobulin G (IgG) derived from human plasma was purchased from Athens Research and Technology (Athens, GA). Anti-human VEGF165 monoclonal mouse antibody (Anti-VEGF) was obtained from PeproTech (Rocky Hill, New Jersey). Transwell® polyester membranes, 12 mm diameter and pore size of 0.4 #m, were obtained from Corning Incorporated (Corning, NY). Phosphate buffered saline (PBS) with calcium and magnesium was obtained from Gibco (Grand Island, NY). Primary human umbilical vein endothelial cells (HUVECs) from pooled donors, isolated in the absence of defined growth factors without exogenous VEGF, were obtained from Lonza (CC-2519; Basel, Switzerland). MC3T3-E1 subclone 4 murine preosteoblast cells were obtained from ATCC (Manassas, VA). CellTracker™ Red CMTPX was obtained from Thermo Fisher Scientific (Waltham, MA). PureCol® Type I bovine collagen was purchased from Advanced BioMatrix (San Diego, CA). Cell Counting Kit-8 (CCK-8) Cell Proliferation and Cytotoxicity Assay was purchased from Dojindo Molecular Technologies (Rockville, MD).

Gel Formation

Previously lyophilized polymers were dissolved in PBS as specified weight percents and allowed to dissolve overnight while mixing in 50 mL Falcon tubes. Chitosan (CS) and hyaluronic acid (HA) were dissolved at 2 wt % and irradiated alginate (IA) was dissolved at 15, 10, and 7.5 wt %.

Solutions were loaded into 3 mL syringes, as noted in Table 1, and mixed rapidly for 10 seconds using a Luer lock before being injected to the desired location.

TABLE 1

Hydrogel Formation Solutions

|  | Syringe 1 | Syringe 2 |
| --- | --- | --- |
| PEC | 833 μL CS | 167 μL 10 wt % IA |
| PEC w/ HA | 750 μL CS, 100 μL HA | 150 μL 10 wt % IA |
| 7.5 wt % IA | 160 μL CaSO4 | 1 mL 7.5 wt % IA |
| 7.5 wt % IA w/ 1 wt % HA | 160 μL CaSO4, 500 μL HA | 500 μL 15 wt % IA |

40 μL of chitosan microgels were added to Syringe 1 using a 1:1 microgel dilution in water for additional experiments.

Microgel Fabrication

Chitosan (ChitoClear™) was added to a 6% acetic acid solution (1.6 grams per 40 mL—4%) and allowed to dissolve for 3 hours at 40° C. covered with mixing. Genipin was dissolved in ethanol at a concentration of 100 mM and allowed to dissolve.

2 mL of 100 mM Genipin were added to the 40 mL solution and mixed in with a spatula briefly. Mixing was allowed to continue for 10 minutes with air exposure, then covered and allowed to mix overnight at 40° C. The solution will thicken enough to stop the stir bar.

The chitosan bulk gel was then pressed through a 250 μm sieve onto a 106 μm sieve giving a particle range of 106-250 μm. The microgels were spun down at 2000 rpm for 5 minutes and re-suspended in Millipore water at a 1:1 dilution for storage and future use.

Rheology

Rheological measurements of hydrogels were determined using an AR-G2 Rheometer with a 20 mm crosshatched geometry attachment set at a loading gap of 1750 μm. Alginate-chitosan hydrogels were prepared as above and refrigerated until being loaded onto the rheometer. For each run, a solvent trap was placed over the plate to ensure that the hydrogel remained at a constant humidity during experimentation. Oscillatory strain sweep experiments were performed at a frequency of 1 Hz by varying the strain rate from 0.1% to 100% after a two-hour incubation period at 37° C., and the storage and loss moduli were recorded. In order to analyze hydrogel gelation and guarantee that at least 90% of gelation had occurred, time sweeps were performed. Time sweep experiments were run for up to eight hours at a constant strain rate of 0.4%, a value within the linear range of the moduli, and storage and loss moduli were recorded.

Permeability

Permeability experiments were performed as previously described (Fletcher, et al., Materials Science and Engineering: C 59, 801, 2016; Wufsus, et al., Biophysical Journal 104, 1812, 2013). Briefly, plastic 3 mL syringes were utilized as permeation chambers by removing the top barrel and coating the syringe with a 0.1% polyethyleneimine (PEI) solution. The various gels were formed in the PEI coated syringes and allowed to gel at 37° C. The length of the gels were measured and the top of the syringe was connected to a reservoir of DI water with tubing. 1/16" tubing was attached to the tip of the syringe and primed with DI water to form a contiguous wetted area. The tubing was lined up with a ruler and the air-water interface was recorded over time to determine the volumetric flow. The permeability of each gel was calculated using Darcy's Law ($v=-k\Delta P/\mu$, v is interstitial velocity, k is permeability, u is viscosity of percolation fluid, and P is pressure).

Rat Physeal Injury Model

All animal procedures were approved by the University of Colorado Denver Institutional Animal Care and Use Committee. Six-week old Sprague-Dawley rats underwent a proximal tibial physeal drill-hole injury as previously described (Erickson, et al., Journal of visualized experiments: JoVE 2017.) Briefly, bilateral 2 mm central drill-hole defects were created using a dental bur, and injected with ~25 μl of the following PEC hydrogel preparations: (1) 90:10+Ca, (2) 50:50+Ca, (3) 50:50−Ca, or (4) IA (n=4 limbs/group) using an 18 gauge blunt end needle. Animals were administered analgesics and were allowed to bear weight immediately after injury.

To compare the repair tissue between the different groups over time, animals were euthanized at days 7, 14, and 28 post-injury. These study end points were chosen based on previously reported studies that have examined repair tissue in untreated animals and found that it consists of dense fibrous tissue at day 7, a mix of fibrous tissue and a developing bony bar at day 14, and a mature bony bar complete with hematopoietic tissues at day 28. After euthanasia, tibiae were excised, fixed in 10% formalin for 4 days, decalcified in 14% EDTA for two weeks, sectioned at 5 μm in a sagittal plane, and stored on Superfrost+slides for histological analysis.

Alcian Blue Hematoxylin Histology

To assess physeal repair tissue and in vivo hydrogel behavior, 3-4 sections approximately 100 μm apart and capturing the center of the physeal injury were stained for histological analysis. Deparaffinized sections were stained with alcian blue/hematoxylin/eosin (ABH), which stains cartilage blue, bone bright orange, fibrous tissue bright pink, and hematopoietic/marrow tissues dark purple. Images were taken using a Nikon microscope, and a region of interest was drawn around the physeal injury site. Images were analyzed using Nikon NIS Elements software to determine the proportion of the repair tissue that was composed of cartilage, fibrous, bone, and marrow tissues. These tissue types are distinguished based of their morphologies and colors. The measurements on four separate sections for each sample were averaged and expressed as percentages of the total injury site area. The drill track area below the physeal injury site was also analyzed to further assess the hydrogels in this environment.

Statistical Calculations

Data is reported as mean±standard error of the mean and comparison between groups were performed with one-way or two-way ANOVA and Tukey post-hoc analysis (Sigma Stat). Statistical significance was determined by $P<0.05$.

Example 1: Antibody Release from Alginate-Chitosan

Alginate-chitosan PECs were formed using solutions of 2 wt % alginate in PBS, 2 wt % chitosan salt in PBS, a calcium sulfate slurry solution (105 mg/mL in ultrapure water), and either an IgG solution (4.03 mg/ml in ultrapure water) or an anti-VEGF solution (5 mg/mL in ultrapure water). PECs were prepared by placing 0.5 mL of alginate solution with 120 μL of ultrapure water (for controls) or 118.6 μL of IgG solution (with 1.4 μL of ultrapure water) or 90 μL of anti-VEGF solution (with 30 μL of ultrapure water) into one 3 mL syringe, and 0.5 mL of chitosan solution with 40 μL of calcium sulfate slurry in a second 3 mL syringe. The two syringes were then connected by a Luer lock adapter and mixed rapidly for 10 seconds. The mixed solution was transferred to a 1 ml syringe and 2 00 μL aliquots were measured into four Transwell membranes and placed into the center row of a 12-well plate. 1 mL of PBS was then added to all wells of the 12-well plate prior to the plate being placed in an incubator (humidified, 37° C., and 5% CO2). Every 5 days, release samples were taken by collecting the PBS from each well and replacing it with fresh PBS. The released antibody in each sample was measured via the microBCA protein assay (Pierce, Grand Island, NY) as per the manufacturer's instructions using known quantities of IgG and anti-VEGF for the standard curves.

Figure 1:
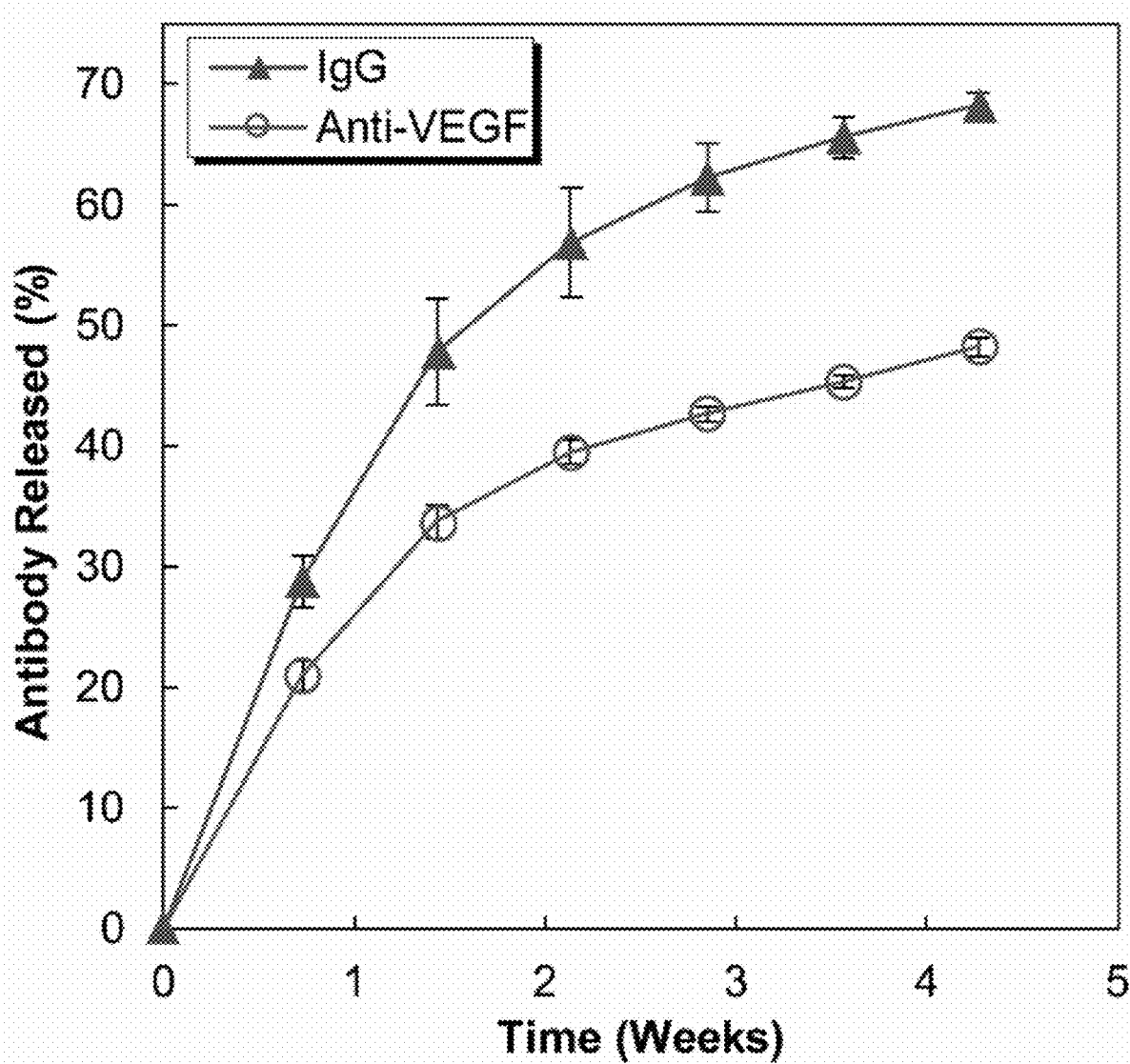
FIG. 1 is a graph of the percent of total antibody loaded in alginate-chitosan PECs that was released over 30 days.

Anti-human VEGF antibodies (anti-VEGF) and nonspecific IgG antibodies derived from human blood plasma (IgG) were released from separate alginate-chitosan PECs (FIG. 1). Although the release curve trend was similar, the anti-VEGF antibodies were found to release at a reduced rate and quantity compared to the nonspecific IgG antibodies (approximately 70% compared to the IgG at each timepoint). The release is quicker during the first 15 days and then slows, but the antibodies continue to show sustained release out to at least 30 days.

The release profiles in FIG. 1 display a higher initial rate of release, followed by a lower, sustained release out to 30 days. The IgG release is consistently faster compared to the anti-VEGF release; without being limited to any particular theory, it is possible that the nature of the antibody determines the electrostatic interactions with the chitosan resulting in different release rates. Anti-VEGF (bevacizumab) has a pronounced negative effective net charge, while model IgG is a mixture of antibodies that has a range of effective net charges. The significant net negative charge results in strong electrostatic interactions between the anti-VEGF and the positively charged chitosan chains, resulting in a slower release rate relative to IgG.

Example 2: Cell Culture

Prior to experiments, HUVECs at passage 3 were thawed, seeded, and cultured for 3 days in endothelial growth medium (EGM, CC-3156, Lonza) containing 2% fetal bovine serum (FBS), bovine brain extract, and growth supplements (CC-4133, Lonza) with no exogenous VEGF. Then the medium was replaced with starvation medium (EGM containing 1% FBS and no growth supplements) for 24 hours. The starvation medium was then removed and replaced with 3 mL of 10 μM CellTracker™ Red in EGM and incubated at 37° C. (humidified with 5% CO2) for 30 minutes. Cells were then passaged and used for cell proliferation and in vitro angiogenesis assays described in later sections.

Example 3: Release-Conditioned Media

Alginate-chitosan PECs with anti-VEGF or water (for controls) were formed by the same procedure as described in Example 1. The Transwell membranes containing the PECs were placed in 12-well plates. Starvation medium was placed in the wells below four of the eight control PECs, while starvation medium with 50 ng of VEGF added was placed in the wells below the four remaining control PECs and the four anti-VEGF PECs. This medium was collected every five days for cell proliferation and in vitro angiogenesis assay experiments (described in the following sections), then replaced with fresh medium of the same type.

Example 4: HUVEC Proliferation

Every 5 days, 200 μL of conditioned media from each well (see Release-Conditioned Media) was moved to a 48 well plate where the well was coated with type I collagen. On day five 4×105 HUVECs/mL starvation medium were added to each well. After considering the results of day five it was determined that more cells would improve experiment clarity and 8×105 HUVECs/mL starvation medium were added to each well for all remaining time points. Cells were then cultured for two days in a humidified incubator at 37° C. and 5% CO2. The CCK-8 assay was used to measure cell proliferation, where the reported values are absorbance measurements minus the absorbance of CCK-8 in starvation medium (day five values were normalized by initial seeding density).

Figure 2:
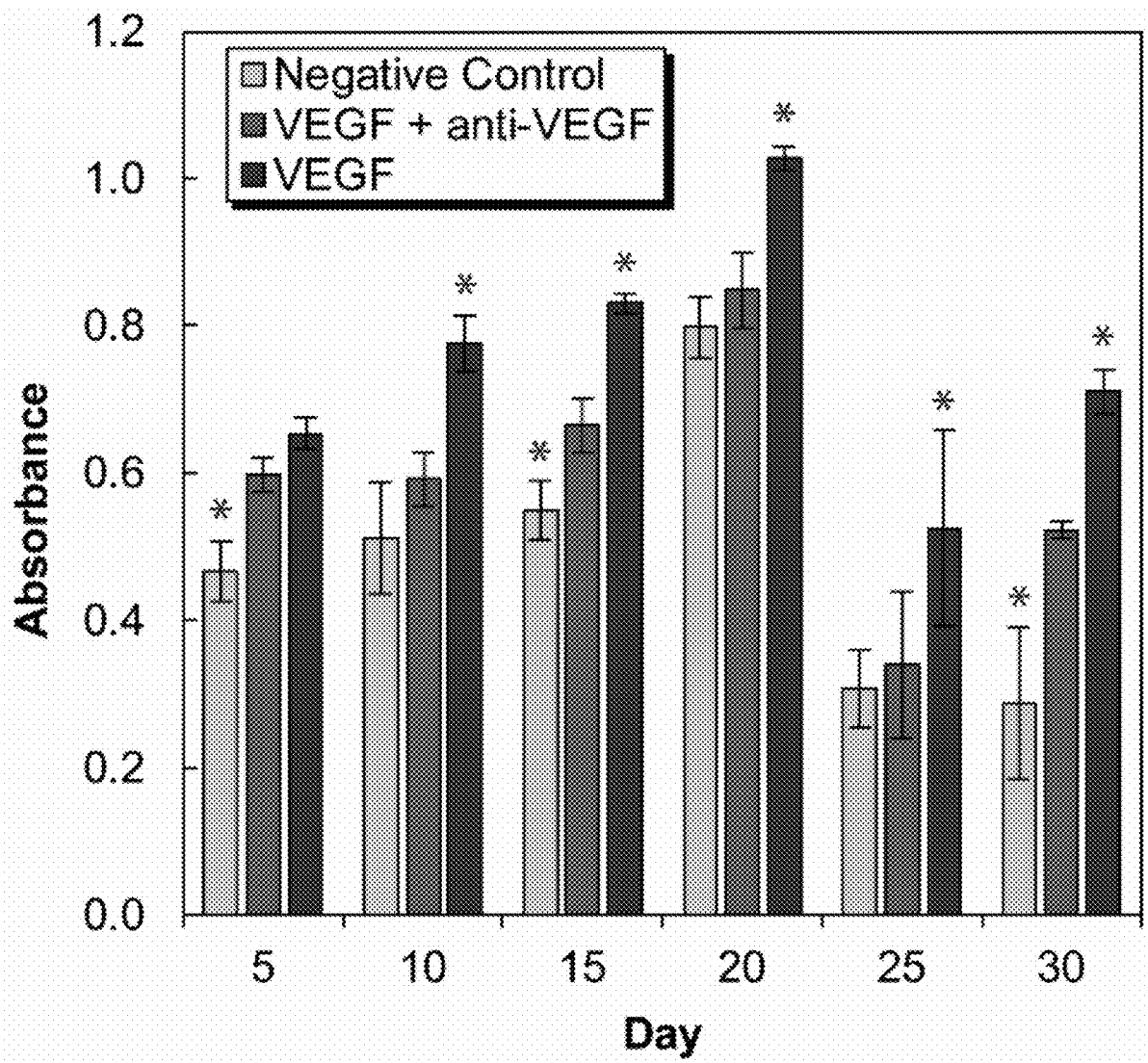
FIG. 2 is a graph showing the proliferation of HUVECs in cell culture medium conditioned by exposure to alginate-chitosan PECs every five days over a 30-day period. Light blue bars are the negative controls (medium without VEGF), dark blue are the positive controls (medium with 50 ng/mL VEGF), both of which were conditioned by blank PECs (without anti-VEGF antibody). The red bars show the experimental group (medium with 50 ng/mL VEGF) and were exposed to PECs loaded with anti-VEGF antibody.

Medium conditioned by exposure to antibody-laden alginate-chitosan PECs were tested for its effect on HUVEC proliferation every five days for one month (FIG. 2). For these studies, there were two control groups: a negative control of HUVECs cultured in starvation medium exposed to blank alginate-chitosan PECs (without antibody), and a positive control of HUVECs cultured in starvation medium with 50 ng/mL VEGF added also exposed to blank alginate-chitosan PECs (without antibody). These were compared to the experimental group, which consisted of HUVECs cultured in starvation medium with 50 ng/mL VEGF added exposed to PECs loaded with anti-VEGF antibody. A statistically significant decrease in proliferation of HUVECs exposed to the anti-VEGF was observed compared to the positive control for all time points out to 30 days except at day 5. Additionally, at days 10, 20, and 25, there is no significant difference between the negative control and the anti-VEGF treated cells, indicating that all VEGF present is bound by the anti-VEGF and unable to influence the cells. Samples from days 10-25 all show the experimental group being closer to the negative control than the positive control.

Example 5: In Vitro Angiogenesis Assay

Every 5 days, 600 μL of conditioned medium from each well (see Example 3) was moved to a 48 well plate that contained a 175 μL type I collagen gel that covered the bottom of each well (gels formed per instructions from Advanced Biomatrix, with 8 parts 3 mg/mL collagen type I, 1 part 10×PBS, then adjusted to pH 7.2-7.4 with 1 part 0.2 M NaOH and ultrapure water). The plates were then placed into the 37° C. incubator for 1 hr before removing 400 μL of the conditioned medium. This was done to allow the conditioned medium to diffuse into the type I collagen gels. Then, 8×105 HUVECs/mL starvation medium were added to each well. Cells were incubated in a humidified environment at 37° C. and 5% CO2 for 12 hrs. At this point the medium from each well was removed and replaced with PBS. Fluorescent images of the cells were taken on a Nikon Eclipse TE 2000-S microscope with a Lumenera infinity 3-1UM camera. Total tubule length was calculated using ImageJ software.

The bioactivity of the anti-VEGF released from the alginate-chitosan PEC (50:50) was examined for its ability to prevent VEGF induced angiogenesis by HUVECs in vitro over the course of 30 days. Representative images of HUVECs on type I collagen gels after 12 hours of exposure to the different types of conditioned medium are shown in FIG. 3. All negative controls (without VEGF and without anti-VEGF) show very few cells with minimal connectivity that are only present in small clusters. Positive control samples (with VEGF but without anti-VEGF exposure) have a greater number of cells covering the collagen surface at all timepoints; they also show substantial interconnection between cell clusters that are present throughout the entire field-of-view. The experimental groups that were exposed to both VEGF and released anti-VEGF from the PECs show similar cell populations as the positive controls, however the cell clusters are larger and less interconnected. This indicates that the anti-VEGF released from the PEC is inhibiting the HUVECs' ability to form tubules with one another. The total tubule length (sum of length of all the tubules in the field of view) formed by the HUVECs for each condition was then quantified in ImageJ (FIG. 4A). For all time points, the experimental group (with VEGF and with anti-VEGF) show less total tubule formation than the positive control group (with VEGF but without anti-VEGF); and for all days, except days 20 and 30, this reduction in total tubule formation is statistically significant. All days show a significant difference between the experimental group and the negative control except for day 25.

VEGF induces proliferation and tube formation of endothelial cells to create new vasculature; this process contributes to the progression of diseases including cancer and macular degeneration. Anti-VEGF antibodies have been demonstrated to inhibit these endothelial cell functions, and anti-VEGF is in clinical use and clinical trials for the treatment of various disease states due to its promise. The ability to provide local, sustained delivery of this antibody over time could further aid in its clinical implementation. In order to demonstrate bioactivity after encapsulation and maintenance at 37° C. in a buffered solution for a long period of time by verifying that anti-VEGF released from the PECs, even out to 30 days, could inhibit the increase of proliferation that endothelial cells exhibit in the presence of VEGF. At several of these time points, there was no statistical difference between the experimental and negative control groups, indicating that the VEGF-induced proliferation was entirely inhibited. Endothelial cell tube formation was characterized by a two-dimensional in vitro angiogenesis assay. Tube formation can be seen in the fluorescent microscopy images in FIG. 3 and statistical analysis of tube formation can be seen in FIG. 4A. Generally, the negative control group, which contained no VEGF in the medium, resulted in a lower number of cells in small clusters with negligible connections to one another, indicating a relatively low level of angiogenesis. The positive control, which had VEGF added to the medium, shows VEGF induced tube formation as indicated by an increased concentration of cells that were highly interconnected and distributed across the surface. The experimental group, which had VEGF added and was exposed to anti-VEGF from the PEC, had a larger number of cells than the negative control. However, they were growing in large clusters with a lower amount of connections between them compared to the positive control, indicating that VEGF induced tube formation was partially inhibited. These qualitative claims were confirmed by quantitative image analysis determining the total tubule length found in each image (FIG. 4A). Anti-VEGF released from the PECs successfully inhibited the VEGF-induced tube formation, as indicated by the experimental group falling between the negative and positive controls for total tubule length at all time points. The reduction in total tubule length of the experimental group compared to the positive control is statistically significant at all time points, except for days 20 and 30, indicating that the anti-VEGF released from the PEC successfully binds soluble VEGF present in the medium to inhibit tube formation. For day 20, the total tubule length of the experimental group nearly reaches that of the positive control group. This was caused by a cell counting error that resulted in increased cell seeding density for day 20 experiments; this conclusion is supported by increased values in the proliferation data (FIG. 2). Through qualitative observation, it is expected that the increased cell seeding density produced overlapping cell clusters which were quantified as increased tubule length but do not demonstrate true connectivity like that seen in the positive control group. Based on 2-D angiogenesis images and quantitative analysis of tubule formation length, anti-VEGF release from alginate-chitosan PECs can successfully inhibit VEGF-induced angiogenesis of HUVECs in vitro.

Additional anti-VEGF release experiments were conducted where alginate and chitosan were mixed together in different ratios. This testing revealed two systems that released anti-VEGF at different rates: alginate:chitosan mixed together in 90:10 and 50:50 ratios. For the in vitro release test, 90:10 was shown to release anti-VEGF quickly while 50:50 released anti-VEGF in a slower, more sustained rate (FIG. 4B).

Example 6: Delivering an Anti-VEGF Ab Reduces Bony Repair Tissue

PECs of various compositions, both with and without anti-VEGF Antibody were tested for their effect on bone repair as measured by bone volume fraction at an injury site. Selected results are shown in FIG. 5.

Example 7: Chitosan Microgels Comprising BM-MSC Chemoattractants

CS was irradiated (I-CS) to 5 Mrad total dose at 220 krad/hr with Cobalt-60 irradiation (Michigan Memorial Phoenix Project, Univ. of Michigan, USA). CS and I-CS were purified separately by dissolving 10 g in 1 L of 1% acetic acid solution, followed by vacuum filtration through a 2.7 µm cellulose paper filter (GE Healthcare, Marlborough, MA) and a 0.45 µm PES membrane filter (Thermo Scientific). The solution was dialyzed (MWCO 3500; Fisher Scientific) for 4 days against diH2O before the retentate was adjusted to pH 8.0 with 1 M NaOH and the polymer was separated by centrifugation (4000×g, 5 min). The pellet was repeatedly re-suspended in diH2O and centrifuged until the supernatant was less than pH 7.2. The purified CS and I-CS were then lyophilized and stored in a desiccator prior to use.

CS and I-CS were dissolved in 0.5 M acetic acid/0.2 M sodium acetate buffer (pH 4.2) at concentrations between 0.8 and 10 mg/mL and intrinsic viscosity was measured with an Ubbholde viscometer (Schott-Gerate, No. II; Mainz, Germany). Mark-Houwink Parameters (K=3.5×10−4 and a=0.76) were applied to determine molecular weight. Fourier Transform Infrared (FTIR) spectroscopy was performed on CS and I-CS using a Nicolet NEXUS 470 FTIR (Thermo) equipped with a Specac Attenuating Total Reflectance (ATR) attachment (Golden Gate; Kent, UK). Potentiometric titrations of CS and I-CS were performed by dissolving 50 mg in 50 mL of 10 mM HCl/1 mM NaCl and titrating with 0.101 M NaOH. Light transmittance measurements at 600 nm on CS and I-CS solutions (1 wt %) were performed at pH 6.0, 6.8, 7.4, and 8.0 (n=3) using a UV-Vis spectrophotometer (Genesys 10S, Thermo Scientific).

Chitosan/genipin (CS/GP) microgels were formed by an in situ emulsion crosslinking method (recipes shown in Table 2).

TABLE 2

Recipes for CS/GP microgels

| Condition | CS (g) | I-CS (g) | Acetic Acid | GP (µmol) | Ethanol (mL) |
|---|---|---|---|---|---|
| CS-2/GP-5 | 0.2 | 0 | 10 mL, 0.5% | 50 | 0.5 |
| CS-4/GP-5 | 0.2 | 0.2 | 10 mL, 1.0% | 50 | 0.5 |
| CS-6/GP-5 | 0.2 | 0.4 | 10 mL, 1.5% | 50 | 0.5 |
| CS-2/GP-25 | 0.2 | 0 | 10 mL, 0.5% | 250 | 0.5 |
| CS-4/GP-25 | 0.2 | 0.2 | 10 mL, 1.0% | 250 | 0.5 |
| CS-6/GP-25 | 0.2 | 0.4 | 10 mL, 1.5% | 250 | 0.5 |

CS was dissolved at 2, 4, or 6 wt % into 10 mL of 0.5% acetic acid solution by magnetic stirring overnight in a closed container. GP solution (100 or 500 mM; 0.5 mL in ethanol) was added dropwise into the stirring chitosan and allowed to mix for 5 mins. The CS/GP mixture was emulsified by stirring in 90 mL of 5% Span 80 in mineral oil and homogenizing at 6000 RPM for 5 mins (PROScientific). The emulsion was stirred at 650 RPM for 18 hrs in a 40° C. water bath. Then the microgel emulsion was separated to 25 mL aliquots and centrifuged (2000×g, 5 min) to remove the mineral oil phase. The pellet aliquots were further washed by consecutive centrifugation (2000×g, 5 min) and resuspension of the pellet in 40 mL the following: hexane, 50% ethanol in diH2O containing 1% Tween 20, and diH2O (5 times). The microgels were then stored in excess diH2O at 4° C. Prior to experiments, a 1:1 microgel dilution was prepared by mixing 1 mL diH2O per gram hydrated microgel pellet (2000×g, 5 min).

Example 8: Chitosan Microgel Ex Vivo Testing

The chitosan microgel formulations described in Example 7 were tested to measure chemoattractant release in in vitro environments at varying pH. Release of SDF1α or TGF-β3 from chitosan microgels in vitro was determined by ELISA (FIG. 6B). SDF1α and TGF-β3 were released from chitosan microgels as a burst release during the first 7 days To test whether the released SDF1α leads to cell recruitment, 12 mm osteochondral explants were harvested from 3-week-old calves and a 4 mm central defect was filled with chitosan microgel+/−SDF1α (FIG. 7). After 3 and 15 days in culture (n=3/day), explants were stained with calcein AM (green) and visualized using confocal microscopy (FIGS. 8A-8C). Cell migration was determined by counting calcein positive cells within the defect area. Images and cell counts from the ex vivo migration study indicate that chitosan microgels containing SDF1α promoted greater cell migration than the empty microgel after 15 days in culture (FIG. 8C, *p<0.05). Selected results are shown in FIGS. 6A-8C.

Example 9: Chitosan Microgel In Vivo Testing

The chitosan microgel formulations described in Example 7 were tested in vivo. A 2 mm centrally located drill-hole defect was created in the proximal tibial growth plate of 6-week-old Sprague-Dawley rats. After rinsing with saline, the injury was treated as follows: group 1, untreated; group 2, chitosan microgel only; group 3, chitosan microgel containing SDF1α; group 4, chitosan microgel containing TGF-β3. After euthanasia on days 7 (n=3/group) and 27 (n=6/group), tibiae were excised. Bone formation at the injury site was assessed by microCT (Siemens Inveon) (FIGS. 9C-9G). DICOM files were reconstructed using ImageJ, and after global thresholding the growth plate injury was selected as the region of interest. Bone volume fraction (BVF) within the growth plate injury area was calculated using BoneJ. To further categorize the tissue repair formed, tibiae were processed for histology and sections stained with alcian blue-hematoxylin (ABH), or immunostained for collagen II and collagen X. Immunostaining for vimentin was used to assess mesenchymal cell infiltration into the repair site. Data is reported as mean+/−standard error of the mean and comparison between groups were performed with one-way ANOVA and Tukey post-hoc analysis (Sigma Stat).

MicroCT data revealed a significant decrease in BVF within the injury site at 7 days post-surgery compared to the untreated group (FIG. 9C, *p<0.05). A non-significant decrease in BVF was observed at 27 days post-injury in chitosan treated animals (FIG. 9C). ABH staining on repair tissue from 7 days post-injury showed chitosan at the injury site in treated animals. Vimentin staining showed no increase in the number of cells within the defect area in the group receiving SDF1α loaded chitosan microgels. ABH staining on repair tissue from 27 days post-injury revealed bony tissue in all groups, and small amounts of cartilaginous tissue present in a few chitosan-treated animals, regardless of the biological factor incorporated in the microgel (FIGS. 9D-9G). No cartilage tissue was seen in the untreated group. Repair tissue did not stain positive for collagen II or collagen X. Histology also revealed that chitosan was largely absent from the injury site 27 days post-injury.

In vivo, implantation of chitosan microgels into injured growth plates led to decreased BVF at 7 days post-injury, potentially due to the biomaterial serving as an interpositional material. Without being limited to any particular theory, the high density of the chitosan microgel at this time point may have limited cell migration into the injured area. It may also be possible that the lack of increased cell migration in the group receiving chitosan microgel with SDF1α was a result of a delayed release of SDF1α in vivo. By 27 days post-injury, chitosan was not observed at the injury site, suggesting its degradation and associated release of biological factors between days 7 to 27 in this model. Injection of chitosan into the injury site resulted in some cartilage repair tissue. Selected results are shown in FIGS. 9A-9G.

Example 10: Rheology

The storage (G') moduli, which is representative of the amount of energy stored in the material, demonstrates the elasticity of the hydrogels with respect to one another. As seen in FIG. 10A, IA had the highest storage modulus, possibly due to increased electrostatic interactions between it and the chitosan due to less steric hindrances of the shorter alginate polysaccharide chain. 90:10+Ca demonstrated the lowest storage modulus likely due to a lower interaction of the alginate and chitosan due to an abundance of the alginate carboxyl groups compared to the chitosan amine groups. All hydrogel types were significantly different from one another except for 50:50−Ca vs. 90:10+Ca, and 50:50+Ca vs. IA (+Ca indicates the presence of added calcium, −Ca indicates the absence of added calcium).

The loss (G") modulus (FIG. 10B) demonstrates the energy loss of the material through heat and is a measure of how viscous the material being tested is. Loss moduli show similar results to the storage moduli with IA having the highest viscous forces. Interestingly, the 90:10+Ca had the lowest loss modulus and demonstrated an increase in loss modulus at high strain rates which is more indicative of a polymer solution than a gel network. The other hydrogels exhibited a decreasing loss modulus at higher strain rates which corresponds to a breaking up of a gel network. These findings correlate well to the compositions of the hydrogels as both 50:50 mixtures should be a network of charge interactions, whereas 90:10+Ca has a charge imbalance and performs more like a polymer solution. All variations of hydrogel are significantly different from one another, except 50:50−Ca vs. 50:50+Ca.

Example 11: Permeability

The permeability results as measured in vitro are shown in Table 3. 90:10+Ca had the highest permeability, 50:50 irradiated alginate (IA) had the lowest permeability, and 50:50+/−Ca had intermediate permeabilities. In vivo histology results showed abundant cellular infiltration within IA, and almost no cellular infiltration in the 90:10+Ca hydrogel.

TABLE 3

| Permeability (mean ± SDEV) | |
|---|---|
| Material | K (Permeability) |
| 90:10 + Ca | $6.38^{-9} \pm 3.52^{-9}$ |
| 50:50 − Ca | $8.88^{-10} \pm 9.79^{-11}$ |
| 50:50 + Ca | $1.88^{-10} \pm 1.33^{-10}$ |
| 50:50 Irradiated Alginate | $4.18^{-12} \pm 1.01^{-12}$ |

Example 12: Hydrogel Degradation and Appearance at the Physeal Injury Site

The 50:50+Ca and 50:50−Ca groups had very similar degradation rates and appearances and resulted in very similar repair tissue at all timepoints (FIG. 11A). On day 7 at the physeal injury site, hydrogels were present in all groups and had the appearance as follows: 90:10+Ca was solid with no cellular infiltration; IA was largely degraded with a collapsed, amorphous shape and abundant cellular infiltration; both 50:50+Ca and 50:50−Ca were degrading at intermediate rates, and had a spaghetti-like appearance with cells throughout (FIG. 11A). By day 14, 90:10+Ca was still present and undegraded. Both 50:50+Ca and 50:50−Ca were present but degrading, and IA had completely degraded at the physeal injury site. At day 28, hydrogels were absent from the physes of all groups, albeit small remnants within the metaphysis.

Example 13: Repair Tissue at the Physeal Injury Site

As for the physeal injury repair tissue, on day 7 ~80-85% of the tissue present in all groups was classified as fibrous. 90:10+Ca was undegraded and completely blocking tissue formation, except for dense fibrous tissue surrounding the hydrogel. The IA hydrogel was mostly degraded which allowed for abundant cellular infiltration and resulted in loose fibrous connective tissue. The 50:50+Ca and 50:50−Ca hydrogels degraded at an intermediate rate, resulting in loose fibrous connective tissue intermingled with the hydrogels (FIG. 11A). At day 14, the 90:10+Ca group had a well-developing bony bar with significantly more bone and marrow tissues, and significantly less fibrous and cartilage tissues than all other groups, with the hydrogel still present and undegraded (FIG. 11B. IA had more fibrous and less bone/marrow repair tissue than all other groups. The 50:50+Ca and 50:50−Ca groups had developed a mix of bony bar and fibrous tissues, with some hydrogel still present.

By day 28, the 90:10+Ca, 50:50+Ca, and 50:50−Ca treated groups had developed mature bony bars, while IA still remained mostly fibrous with a small amount of bone. The IA treated group had more cartilage (p=0.05 vs. 90:10+Ca only) and fibrous tissues (p<0.05 vs. all groups), and less bone (p<0.05 vs. 90:10+Ca and 50:50−Ca) and marrow tissues (p<0.05 vs. 90:10+Ca and 50:50−Ca) than the other groups (FIG. 11C). No significant differences were detected between the 50:50+Ca and 50:50−Ca groups at any timepoint.

Example 14: Hydrogel Degradation and Appearance in Drill Track

Histology at the drill track showed similar hydrogel degradation patterns to those at the physeal injury site (FIG. 12). At days 7 and 14, the 90:10+Ca hydrogel was undegraded and was blocking cellular infiltration. Tissue surrounding this gel was mostly fibrous. The 50:50+/−Ca hydrogels were degrading and had a spaghetti-like appearance with cells infiltrating throughout the gels and was surrounded by a loose connective tissue. The IA hydrogel was mostly degraded and had abundant cell infiltration and was surrounded by dense connective tissue.

Similar results were seen at day 28. The 90:10+Ca hydrogel was undegraded and completely blocking tissue growth, while the 50:50+/−Ca hydrogels were more degraded with cells throughout. The IA hydrogel was mostly degraded and infiltrated with a dense connective tissue. Interestingly, at day 28 the bone surrounding the drill track within the metaphysis was more pronounced in the 90:10+Ca group, and less pronounced in the 50:50+/−Ca groups. In 90:10+Ca treated animals, this bone had a dense, cortical-like appearance within the drill track. IA, on the other hand was surrounded by fibrous tissue, and by bone of a more porous, trabecular appearance (FIG. 12).

Example 15: Hydrogel Storage Modulus Measurements

As seen in FIG. 13 and FIG. 14, the Irradiated Alginate PECs comprised 5 wt % irradiated (low MW) alginate and 1 wt % chitosan, or 7.5 wt % irradiated alginate and 1 wt % chitosan, +/−hyaluronic acid (HA). The inclusion of HA decreased the storage modulus of the gels. Increasing the wt % of irradiated alginate increased the storage modulus of the gels. The inclusion of chitosan microgels did not have an impact on the storage modulus of these gels. In FIG. 14 additional conditions are demonstrated with the general trend showing that inclusion of HA decreased the modulus of the materials, increasing the wt % of alginate increased the modulus, and heating the PECs did not impact the modulus.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a growth plate injury in a subject, the method comprising administering to the subject, a therapeutically effective amount of a hydrogel composition consisting of at least one hydrogel polymer material selected from the group consisting of chitosan, alginate and a combination thereof, at least one biological factor selected from the group consisting of anti-VEGF compounds, stem cell attracting factors, and transforming growth factor beta cytokines; and optionally hyaluronic acid; and treating the growth plate injury in the subject.

2. The method of claim 1, wherein the hydrogel composition is administered via injection to the subject.

3. The method of claim 2, wherein the hydrogel composition is administered via direct injection to a site of the growth plate injury in the subject.

4. The method of claim 1, wherein, before the administering of the hydrogel composition, a bony bar is surgically removed from a site of the growth plate injury in the subject.

5. The method of claim 1, wherein the hydrogel composition reduces or prevents growth of bony bars in cartilage tissue at a site of the growth plate injury in the subject.

6. The method of claim 1, wherein the hydrogel composition treats or prevents arrest of bone growth at a site of the growth plate injury in the subject.

7. The method of claim 1, wherein the hydrogel composition treats or prevents bone deformities at a site of the growth plate injury in the subject.

8. The method of claim 1, wherein the subject is a mammal.

9. The method of claim 8, wherein the mammalian subject is a human.

10. The method of claim 1, wherein the subject is an infant, toddler, child, juvenile, adolescent, or young adult.

11. The method of claim 1, wherein hyaluronic acid is present in the hydrogel composition.

12. The method of claim 1, wherein the hydrogel composition is a hydrogel polyelectrolyte complex (PEC) of chitosan and alginate, wherein the at least one biological factor is embedded within the hydrogel PEC, and wherein the hydrogel PEC is with or without hyaluronic acid.

13. The method of claim 1, wherein the at least one biological factor is a monoclonal antibody raised against VEGF.

14. The method of claim 1, wherein when chitosan is present, the chitosan is a chitosan cross-linked with genipin.

15. The method of claim 1, wherein hyaluronic acid is absent in the hydrogel composition.

16. The method of claim 1, wherein the at least one hydrogel polymer material consists of chitosan and alginate in a 50/50 weight ratio or 10/90 weight ratio of chitosan to alginate.

17. The method of claim 1, wherein the at least one hydrogel polymer material is alginate.

18. A method of treating a growth plate injury in a subject, the method comprising administering to the subject, a therapeutically effective amount of a hydrogel composition consisting of a hydrogel polymer material consisting of chitosan and alginate; at least one biological factor selected from the group consisting of anti-VEGF compounds, stem cell attracting factors, and transforming growth factor beta cytokines; and optionally hyaluronic acid; and treating the growth plate injury in the subject.

19. The method of claim 18, wherein hyaluronic acid is present in the hydrogel composition.

* * * * *